US012228584B2

(12) United States Patent
Chen

(10) Patent No.: US 12,228,584 B2
(45) Date of Patent: *Feb. 18, 2025

(54) MULTI-STAGE SAMPLE RECOVERY SYSTEM

(71) Applicant: XCella Biosciences, Inc., Emeryville, CA (US)

(72) Inventor: Bob Chen, East Palo Alto, CA (US)

(73) Assignee: XCella Biosciences, Inc., Menlo Park, CA (US)

(*) Notice: Subject to any disclaimer, the term of this patent is extended or adjusted under 35 U.S.C. 154(b) by 712 days.

This patent is subject to a terminal disclaimer.

(21) Appl. No.: 17/506,600

(22) Filed: Oct. 20, 2021

(65) Prior Publication Data

US 2022/0043017 A1     Feb. 10, 2022

Related U.S. Application Data

(63) Continuation of application No. 15/853,332, filed on Dec. 22, 2017, now Pat. No. 11,156,626.

(Continued)

(51) Int. Cl.
*G01N 35/10*     (2006.01)
*B01J 19/00*     (2006.01)
(Continued)

(52) U.S. Cl.
CPC .......... *G01N 35/10* (2013.01); *B01J 19/0046* (2013.01); *B01L 3/502715* (2013.01);
(Continued)

(58) Field of Classification Search
None
See application file for complete search history.

(56) References Cited

U.S. PATENT DOCUMENTS 4,004,150 A    1/1977  Natelson
4,017,185 A    4/1977  Chupp
(Continued)

FOREIGN PATENT DOCUMENTS

AU    6027873    3/1975
AU    6174673    4/1975
(Continued)

OTHER PUBLICATIONS

Carl Zeiss, 2007, Objective LD "Plan-Neofluar" 40x/0.6 Corr www.micro-shop.zeiss.com Mar. 13, 2007, 2 pp.
(Continued)

*Primary Examiner* — Neil N Turk
*Assistant Examiner* — Benjamin Joseph Kass
(74) *Attorney, Agent, or Firm* — Knobbe, Martens, Olson & Bear, LLP

(57) ABSTRACT

Multi-stage sample-recovery systems, including automated 2-stage and 3-stage sample-recovery systems, are provided. Such systems enable the rapid screening and recovery of samples, including viable cell-based samples, from high-throughput screening systems, including systems utilizing large-scale arrays of microcapillaries. In specific screening systems, each microcapillary comprises a solution containing a variant protein, an immobilized target molecule, and a reporter element. Immobilized target molecules may include any molecule of interest, including proteins, nucleic acids, carbohydrates, and other biomolecules. The association of a variant protein with a molecular target is assessed by measuring a signal from the reporter element. The contents of microcapillaries identified in the assays as containing variant proteins of interest can be identified and recovered using the multi-stage systems disclosed herein.

24 Claims, 12 Drawing Sheets

Related U.S. Application Data

(60) Provisional application No. 62/441,128, filed on Dec. 30, 2016.

(51) Int. Cl.
*B01L 3/00* (2006.01)
*B01L 9/00* (2006.01)
*C12N 15/10* (2006.01)
*C12Q 1/6851* (2018.01)
*C40B 60/02* (2006.01)
*G01N 15/14* (2006.01)
*G01N 15/1433* (2024.01)
*G01N 21/75* (2006.01)
*G01N 33/543* (2006.01)
*G01N 15/10* (2006.01)
*G01N 21/03* (2006.01)
*G01N 21/64* (2006.01)
*G01N 21/77* (2006.01)
*G01N 35/00* (2006.01)

(52) U.S. Cl.
CPC ........... *B01L 3/50857* (2013.01); *B01L 9/523* (2013.01); *C12N 15/1003* (2013.01); *C12Q 1/6851* (2013.01); *C40B 60/02* (2013.01); *G01N 15/1433* (2024.01); *G01N 15/1484* (2013.01); *G01N 21/75* (2013.01); *G01N 33/54386* (2013.01); *B01J 2219/00306* (2013.01); *B01J 2219/00509* (2013.01); *B01J 2219/00511* (2013.01); *B01J 2219/00524* (2013.01); *B01J 2219/00587* (2013.01); *B01J 2219/00599* (2013.01); *B01J 2219/00684* (2013.01); *B01J 2219/00722* (2013.01); *B01J 2219/00869* (2013.01); *B01J 2219/0097* (2013.01); *B01L 2200/0668* (2013.01); *B01L 2200/142* (2013.01); *B01L 2300/0816* (2013.01); *B01L 2300/0829* (2013.01); *B01L 2300/0893* (2013.01); *C12Q 2531/113* (2013.01); *G01N 2015/1006* (2013.01); *G01N 2021/0346* (2013.01); *G01N 21/6428* (2013.01); *G01N 2021/6439* (2013.01); *G01N 2021/755* (2013.01); *G01N 2021/7769* (2013.01); *G01N 2035/00158* (2013.01); *G01N 2035/1039* (2013.01); *G01N 2035/1053* (2013.01)

(56) References Cited

U.S. PATENT DOCUMENTS

| | | |
|---|---|---|
| 4,111,754 A | 9/1978 | Park |
| 4,498,782 A | 2/1985 | Proctor et al. |
| 4,621,059 A | 11/1986 | Rokugawa |
| 4,762,420 A | 8/1988 | Bowley |
| 4,960,566 A | 10/1990 | Mochida |
| 4,968,148 A | 11/1990 | Chow et al. |
| 5,072,382 A | 12/1991 | Kamentsky |
| 5,073,029 A | 12/1991 | Eberly et al. |
| 5,112,134 A | 5/1992 | Chow et al. |
| 5,262,129 A | 11/1993 | Terada et al. |
| 5,265,169 A | 11/1993 | Ohta et al. |
| 5,389,555 A | 2/1995 | Watanabe et al. |
| 5,675,155 A | 10/1997 | Pentoney et al. |
| 5,730,187 A | 3/1998 | Howitz et al. |
| 5,763,263 A | 6/1998 | Dehlinger |
| 5,766,875 A | 6/1998 | Hafeman et al. |
| 5,774,214 A | 6/1998 | Prettyjohns |
| 5,843,767 A | 12/1998 | Beattie |
| 5,854,684 A | 12/1998 | Stabile et al. |
| 6,027,873 A | 2/2000 | Schellenberger et al. |
| 6,071,748 A | 6/2000 | Modlin et al. |
| 6,143,496 A | 11/2000 | Brown et al. |
| 6,174,673 B1 | 1/2001 | Short et al. |
| 6,246,525 B1 | 6/2001 | Ikami |
| 6,306,578 B1 | 10/2001 | Schellenberger et al. |
| 6,345,115 B1 | 2/2002 | Ramm et al. |
| 6,377,721 B1 | 4/2002 | Walt et al. |
| 6,387,331 B1 | 5/2002 | Hunter et al. |
| 6,436,632 B2 | 8/2002 | Schellenberger et al. |
| 6,441,973 B1 | 8/2002 | Walt et al. |
| 6,496,309 B1 | 12/2002 | Bliton et al. |
| 6,544,480 B1 | 4/2003 | Velghe et al. |
| 6,547,941 B2 | 4/2003 | Kopf et al. |
| 6,586,257 B1 | 7/2003 | Vuong |
| 6,716,629 B2 | 4/2004 | Hess et al. |
| 6,743,633 B1 | 6/2004 | Hunter |
| 6,794,127 B1 | 9/2004 | Lafferty et al. |
| 6,816,257 B2 | 11/2004 | Goix |
| 6,823,079 B1 | 11/2004 | Winterot et al. |
| 6,838,680 B2 | 1/2005 | Maher et al. |
| 6,866,824 B2 | 3/2005 | Lafferty et al. |
| 6,881,312 B2 | 4/2005 | Kopf et al. |
| 6,893,877 B2 | 5/2005 | Hunter et al. |
| 6,907,798 B2 | 6/2005 | Ganser et al. |
| 6,972,183 B1 | 12/2005 | Lafferty et al. |
| 6,977,723 B2 | 12/2005 | Lemmo et al. |
| 7,012,676 B2 | 3/2006 | Baer et al. |
| 7,019,827 B2 | 3/2006 | Laffert |
| 7,105,132 B2 | 9/2006 | Shumate et al. |
| 7,145,645 B2 | 12/2006 | Blumenfeld et al. |
| 7,221,455 B2 | 5/2007 | Chediak et al. |
| 7,272,510 B2 | 9/2007 | Hansen et al. |
| 7,282,329 B2 | 10/2007 | Manalis et al. |
| 7,289,217 B2 | 10/2007 | Boege et al. |
| 7,387,891 B2 | 6/2008 | Boege et al. |
| 7,403,280 B2 | 7/2008 | Beigel et al. |
| 7,452,507 B2 | 11/2008 | Renzi et al. |
| 7,547,556 B2 | 6/2009 | Hunter et al. |
| 7,666,360 B2 | 2/2010 | Schellenberger et al. |
| 7,666,630 B2 | 2/2010 | Yaver et al. |
| 7,738,945 B2 | 6/2010 | Fauver et al. |
| 7,807,108 B2 | 10/2010 | Fasulka |
| 7,907,259 B2 | 3/2011 | Sägmüller et al. |
| 7,933,004 B2 | 4/2011 | Sugita |
| 8,029,745 B2 | 10/2011 | Hunter et al. |
| 8,278,071 B2 | 10/2012 | Brown et al. |
| 8,309,035 B2 | 11/2012 | Chen et al. |
| 8,325,342 B2 | 12/2012 | Ali et al. |
| 8,338,092 B2 | 12/2012 | Hofmann et al. |
| 8,460,878 B2 | 6/2013 | Walt et al. |
| 8,460,879 B2 | 6/2013 | Walt et al. |
| 8,492,098 B2 | 7/2013 | Walt et al. |
| 8,535,876 B2 | 9/2013 | Wesner |
| 8,551,698 B2 | 10/2013 | Brown et al. |
| 8,623,596 B2 | 1/2014 | Gandini et al. |
| 8,664,002 B2 | 3/2014 | Yeung |
| 8,673,218 B2 | 3/2014 | Jaffe et al. |
| 8,679,853 B2 | 3/2014 | Bhullar et al. |
| 8,722,357 B2 | 5/2014 | Baer et al. |
| 8,785,883 B2 | 7/2014 | Nakazawa et al. |
| 8,829,426 B2 | 9/2014 | Vertes et al. |
| 8,936,762 B2 | 1/2015 | Ehrlich et al. |
| 9,151,713 B2 | 10/2015 | Fan et al. |
| 9,314,764 B2 | 4/2016 | Hess et al. |
| 9,404,152 B2 | 8/2016 | Hasson et al. |
| 9,657,290 B2 | 5/2017 | Dimov et al. |
| 9,908,115 B2 | 3/2018 | Hobbs et al. |
| 10,087,408 B2 | 10/2018 | Hansen et al. |
| 10,227,583 B2 | 3/2019 | Cochran et al. |
| D844,471 S | 4/2019 | Stone |
| 11,085,039 B2 | 8/2021 | Cochran et al. |
| 11,156,626 B2 | 10/2021 | Chen |
| 11,473,081 B2 | 10/2022 | Cochran et al. |
| 2002/0045270 A1 | 4/2002 | Schurenberg et al. |
| 2002/0086322 A1 | 7/2002 | Yu |
| 2003/0003500 A1 | 1/2003 | Lafferty et al. |
| 2003/0044968 A1 | 3/2003 | Lafferty et al. |
| 2003/0092194 A1 | 5/2003 | Gambini |
| 2003/0096220 A1 | 5/2003 | Lafferty et al. |
| 2003/0106997 A1 | 6/2003 | Beecher et al. |

(56) References Cited

U.S. PATENT DOCUMENTS

| | | |
|---|---|---|
| 2003/0143580 A1 | 7/2003 | Straus et al. |
| 2003/0168458 A1 | 9/2003 | Lafferty et al. |
| 2003/0215798 A1 | 11/2003 | Short et al. |
| 2003/0231989 A1 | 12/2003 | Schleifer et al. |
| 2004/0005582 A1 | 1/2004 | Shipwash |
| 2004/0070763 A1 | 4/2004 | Yeung et al. |
| 2005/0057749 A1 | 3/2005 | Dietz et al. |
| 2005/0070005 A1 | 3/2005 | Keller et al. |
| 2005/0079105 A1 | 4/2005 | Hunter et al. |
| 2005/0287044 A1 | 12/2005 | Nataraj |
| 2006/0257013 A1 | 11/2006 | Ramm |
| 2006/0275847 A1 | 12/2006 | Goodyer |
| 2008/0062421 A1 | 3/2008 | Zhou |
| 2009/0042744 A1 | 2/2009 | Wagner et al. |
| 2009/0161100 A1 | 6/2009 | Minot et al. |
| 2010/0008892 A1 | 1/2010 | Shankar et al. |
| 2010/0252748 A1 | 10/2010 | Laitinen |
| 2010/0261159 A1 | 10/2010 | Hess et al. |
| 2011/0049385 A1 | 3/2011 | Laitinen |
| 2011/0124520 A1 | 5/2011 | Love et al. |
| 2011/0251105 A1 | 10/2011 | Walt et al. |
| 2011/0294208 A1 | 12/2011 | Allbritton et al. |
| 2012/0009671 A1 | 1/2012 | Hansen |
| 2012/0013726 A1 | 1/2012 | Thorburn |
| 2012/0015347 A1 | 1/2012 | Singhal |
| 2012/0021951 A1 | 1/2012 | Hess et al. |
| 2012/0064564 A1 | 3/2012 | Grassl |
| 2012/0094851 A1 | 4/2012 | Schellenberger et al. |
| 2012/0204906 A1 | 8/2012 | Bommarito |
| 2012/0244749 A1 | 9/2012 | Xiao |
| 2012/0321419 A1 | 12/2012 | Neeper |
| 2013/0019006 A1 | 1/2013 | Drittler |
| 2013/0190206 A1 | 7/2013 | Leonard et al. |
| 2013/0190212 A1 | 7/2013 | Handique |
| 2013/0196861 A1 | 8/2013 | Quake |
| 2013/0220528 A1 | 8/2013 | Peng et al. |
| 2013/0236905 A1 | 9/2013 | Marshall |
| 2013/0237443 A1 | 9/2013 | Knebel et al. |
| 2013/0260479 A1 | 10/2013 | Chou et al. |
| 2014/0011690 A1 | 1/2014 | Dimov et al. |
| 2014/0017700 A1 | 1/2014 | Fan et al. |
| 2014/0098214 A1 | 4/2014 | Schlaudraff et al. |
| 2014/0147884 A1 | 5/2014 | Schlaudraff et al. |
| 2014/0272984 A1 | 9/2014 | Hasson et al. |
| 2014/0329240 A1 | 11/2014 | Beer et al. |
| 2014/0329305 A1 | 11/2014 | Brown et al. |
| 2015/0051118 A1 | 2/2015 | Ghenciu et al. |
| 2015/0126412 A1 | 5/2015 | Hunter et al. |
| 2015/0323544 A1 | 11/2015 | Cambell et al. |
| 2015/0333471 A1 | 11/2015 | Chimmalgi et al. |
| 2016/0032404 A1 | 2/2016 | Schweighofer et al. |
| 2016/0202150 A1 | 7/2016 | Schlaudraff et al. |
| 2016/0215805 A1 | 8/2016 | Cochran et al. |
| 2016/0244749 A1 | 8/2016 | Cochran et al. |
| 2016/0245805 A1 | 8/2016 | Baer et al. |
| 2016/0305936 A1 | 10/2016 | Leonard et al. |
| 2016/0332133 A1 | 11/2016 | Hess et al. |
| 2018/0163198 A1 | 6/2018 | Cochran et al. |
| 2018/0164294 A1 | 6/2018 | Cochran et al. |
| 2018/0230534 A1 | 8/2018 | Chen et al. |
| 2018/0299379 A1 | 10/2018 | Chen |
| 2018/0363059 A1 | 12/2018 | Quake et al. |
| 2019/0040461 A1 | 2/2019 | Ryu et al. |
| 2019/0094113 A1 | 3/2019 | Huang et al. |
| 2019/0217297 A1 | 7/2019 | Lavieu et al. |
| 2020/0150119 A1 | 5/2020 | Singhal et al. |
| 2020/0316593 A1 | 10/2020 | Chen et al. |
| 2022/0162594 A1 | 5/2022 | Hsien |
| 2022/0373440 A1 | 11/2022 | Chen |
| 2023/0183676 A1 | 6/2023 | Cochran et al. |

FOREIGN PATENT DOCUMENTS

| | | |
|---|---|---|
| CN | 101529304 | 9/2009 |
| CN | 102348807 | 2/2012 |
| CN | 102445750 | 5/2012 |
| CN | 104656379 | 5/2015 |
| EP | 1 207 392 | 5/2002 |
| EP | 1 532 449 | 12/2010 |
| EP | 2 733 673 | 5/2014 |
| EP | 3 473 700 A1 | 4/2019 |
| JP | 2003-319778 | 11/2003 |
| JP | 2004-093558 | 3/2004 |
| JP | 2007-535484 | 12/2007 |
| JP | 2008-200037 | 9/2008 |
| JP | 2010-112955 | 5/2010 |
| JP | 2010-281595 | 12/2010 |
| JP | 2016-163549 | 9/2016 |
| JP | 2018-017657 | 2/2018 |
| JP | 2020-533004 | 3/2019 |
| WO | WO 90/02326 | 3/1990 |
| WO | WO 98/020020 | 5/1998 |
| WO | WO 99/017094 | 4/1999 |
| WO | WO 00/031774 | 6/2000 |
| WO | WO 02/031203 | 4/2002 |
| WO | WO 02/072264 | 9/2002 |
| WO | WO 03/015922 | 2/2003 |
| WO | WO 03/072796 | 9/2003 |
| WO | WO 05/040406 | 5/2005 |
| WO | WO 05/078438 | 8/2005 |
| WO | WO 05/121864 | 12/2005 |
| WO | WO 07/022026 | 2/2007 |
| WO | WO 07/035633 | 3/2007 |
| WO | WO 07/098148 | 8/2007 |
| WO | WO 08/034833 | 3/2008 |
| WO | WO 10/069913 | 6/2010 |
| WO | WO 11/049524 | 4/2011 |
| WO | WO 12/007537 | 1/2012 |
| WO | WO 13/008583 | 1/2013 |
| WO | WO 13/138767 | 3/2013 |
| WO | WO 13/181288 | 12/2013 |
| WO | WO 14/008056 | 1/2014 |
| WO | WO 14/011985 | 1/2014 |
| WO | WO 14/070783 | 5/2014 |
| WO | WO 14/070873 | 5/2014 |
| WO | WO 14/074367 | 5/2014 |
| WO | WO 15/004321 | 1/2015 |
| WO | WO 15/017889 | 2/2015 |
| WO | WO 15/061462 | 4/2015 |
| WO | WO 15/061497 | 4/2015 |
| WO | WO 15/061506 | 4/2015 |
| WO | WO 15/095623 | 6/2015 |
| WO | WO 15/164846 | 10/2015 |
| WO | WO 15/164847 | 10/2015 |
| WO | WO 15/188171 | 12/2015 |
| WO | WO 15/104321 | 2/2016 |
| WO | WO 16/019341 | 2/2016 |
| WO | WO 16/077249 | 5/2016 |
| WO | WO 16/090295 | 6/2016 |
| WO | WO 16/094308 | 6/2016 |
| WO | WO 16/094333 | 6/2016 |
| WO | WO 16/094459 | 6/2016 |
| WO | WO 16/094507 | 6/2016 |
| WO | WO 16/094522 | 6/2016 |
| WO | WO 16/094715 | 6/2016 |
| WO | WO 16/115537 | 7/2016 |
| WO | WO 16/116455 | 7/2016 |
| WO | WO 16/118915 | 7/2016 |
| WO | WO 16/127107 | 8/2016 |
| WO | WO 16/134370 | 8/2016 |
| WO | WO 16/141343 | 9/2016 |
| WO | WO 16/172350 | 10/2016 |
| WO | WO 16/172454 | 10/2016 |
| WO | WO 16/172621 | 10/2016 |
| WO | WO 16/172623 | 10/2016 |
| WO | WO 17/059273 | 4/2017 |
| WO | WO 17/075295 | 5/2017 |
| WO | WO 17/091601 | 6/2017 |
| WO | WO 17/100347 | 6/2017 |
| WO | WO 17/117408 | 7/2017 |
| WO | WO 17/117521 | 7/2017 |
| WO | WO 17/117567 | 7/2017 |
| WO | WO 17/123978 | 7/2017 |
| WO | WO 17/161210 | 9/2017 |

(56) References Cited

FOREIGN PATENT DOCUMENTS

| WO | WO 17/173105 | 10/2017 |
|----|--------------|---------|
| WO | WO 17/176555 | 10/2017 |
| WO | WO 17/181135 | 10/2017 |
| WO | WO 17/205830 | 11/2017 |
| WO | WO 18/018017 | 1/2018  |
| WO | WO 18/053485 | 3/2018  |
| WO | WO 18/119043 | 3/2018  |
| WO | WO 18/064640 | 4/2018  |
| WO | WO 18/076024 | 4/2018  |
| WO | WO 18/102747 | 6/2018  |
| WO | WO 18/102748 | 6/2018  |
| WO | WO 18/102781 | 6/2018  |
| WO | WO 18/111765 | 6/2018  |
| WO | WO 18/126205 | 7/2018  |
| WO | WO 18/200872 | 11/2018 |
| WO | WO 19/015675 | 1/2019  |
| WO | WO 19/075476 | 4/2019  |
| WO | WO 19/133874 | 7/2019  |
| WO | WO 19/191459 | 10/2019 |
| WO | WO 19/232473 | 12/2019 |

OTHER PUBLICATIONS

Chen et al., Feb. 2016, High-throughput analysis and protein engineering using microcapillary arrays, Nature Chem. Biol. 12:76-81.

Chen, Jan. 2015, High-Throughput Analysis and Protein Engineering Using Microcapillary Arrays. A Dissertation Submitted to the Department of Bioengineering and the Committee on Graduate Studies of Stanford University, 190 pp.

Dobes et al., 2013, Laser-Based Directed Release of Array Elements for Efficient Collection into Targeted Microwells, Analyst, 138(3):831-838 with supplemental information.

Dobes Laser-Based Directed Release of Array Elements for Efficient Collection into Targeted Microwells Supplemental Information Analyst, 2013, 138, 831-838 (2013) (Year: 2013).

Emmert-Buck et al., Nov. 8, 1996, Laser Capture Microdissection, Science, 274:998-1001.

Kelkar et al., 2012, Bioluminescence based in vivo screening technologies, Curr. Opin. Pharmacol. 12:592-600.

LEICA LMD6500, LEICA LMD7000 Laser Microdissection Systems, product brochure, 2013, 16 pp.

Michelini et al., 2010, Cell-based assays: fueling drug discovery, Anal. Bioanal. Chem. 398:227-238.

Quiagen, Cignal™ reporter assays, www.sabiosciences.com/reporterassay.php (Accessed Apr. 2017).

Quiagen, NFxB Reporter, http://www.sabiosciences.com/reporter_assay_product/HTML/CCS-013L-html (Accessed Apr. 2017).

Salazar et al., 2007, Micropallet Arrays for the Separation of Single, Adherent Cells, Anal. Chem. 79:682-687.

Vandewoestyne et al., 2013, Laser capture microdissection: Should an ultraviolet or infrared laser be used? Analytical Biochemistry, 439:88-98.

Vogel et al. 2007, Principles of Laser Microdissection and Catapulting of Histologic Specimens and Live Cells, Methods in Cell Biology, 82:153-205.

Cherf, 2015, Applications of yeast surface display for protein engineering, Methods Mol. Biol., 13198:155-175.

Ching et al., Nov. 2, 2017, Chickens with humanized immunoglobulin genes generate antibodies with high affinity and broad epitope coverage to conserved targets, mAbs, 10(1):71-80.

Guild et al., 2011, Wheat germ cell-free expression system as a pathway to improve protein yield and solubility for the SSGCID pipeline, Acta Cryst., F67:1027-1031.

Sasaki, 2006, Structural basis for Fas6-Axl signalling, the EMBO Journal, 25(1):80-87.

Ward's Science, 2012, Beer-Lambert Law: Measuring Percent Transmittance of Solutions at Different Concentrations, Teacher's Guide, downloaded Mar. 28, 2020 from https://www.wardsci.com/www.wardsci.com/images/Beerlamb_Colorimeter.pdf, 21 pp.

International Search Report and Written Opinion dated Jul. 5, 2018 in application No. PCT/US2017/068296.

MULTI-STAGE SAMPLE RECOVERY SYSTEM

CROSS REFERENCE TO RELATED APPLICATION

The present application is a continuation of U.S. patent application Ser. No. 15/853,332, filed Dec. 22, 2017, entitled "MULTI-STAGE SAMPLE RECOVERY SYSTEM," and issued as U.S. Pat. No. 11,556,626, which claims the benefit of U.S. Provisional Application No. 62/441,128, filed on Dec. 30, 2016, entitled "MULTI-STAGE SAMPLE RECOVERY SYSTEM," each of which is expressly incorporated herein by reference.

BACKGROUND OF THE INVENTION

The analysis of biological samples, including the identification, characterization, and re-engineering of proteins, nucleic acids, carbohydrates, and other important biomolecules, has benefited greatly from the scaling up of sample numbers and the scaling down of sample sizes. For example, the two-dimensional microarrays of biological materials, such as DNA microarrays, have enabled the development of high-throughput screening methods involving multiplexed approaches for processing samples and detecting results.

The above approaches have, in some cases, benefited from their combination with optical sensing technology to identify specimens of interest using fluorescent or other corresponding specific and sensitive labeling approaches.

While such techniques provide analytical information about a particular sample, for example the presence and potentially the amount of a particular biomolecule in a solution or the sequence of a particular nucleic acid or polypeptide, they typically do not allow for the recovery of a biological sample identified by the assay without inactivating or otherwise damaging the sample of interest.

There is therefore a continuing need to develop improved microscale screening and analysis methods and systems with high throughput capabilities, and particularly methods and systems that enable recovery of samples identified in the screening and analysis.

SUMMARY OF THE INVENTION

The present disclosure addresses these and other needs by providing in one aspect multi-stage sample recovery systems comprising:
  a screening array stage, wherein the screening array stage is controllable in two dimensions relative to a microscope objective and is configured for reversible association with a screening array; and
  a first recovery array stage, wherein the first recovery array stage is controllable in at least one dimension relative to the microscope objective and is configured for reversible association with a recovery array;
  wherein the screening array stage and the first recovery array stage are controllable independently of one another.

In some embodiments, the multi-stage sample recovery systems of the instant disclosure further comprise a screening array reversibly associated with the screening array stage and a recovery array reversibly associated with the first recovery array stage.

In some embodiments, the systems further comprise an extraction beam generator optically coupled through an aperture in the screening array stage to a microscale sample vessel in the screening array.

In some embodiments, the systems further comprise a second recovery array stage.

DETAILED DESCRIPTION OF THE INVENTION

Figure 1A:
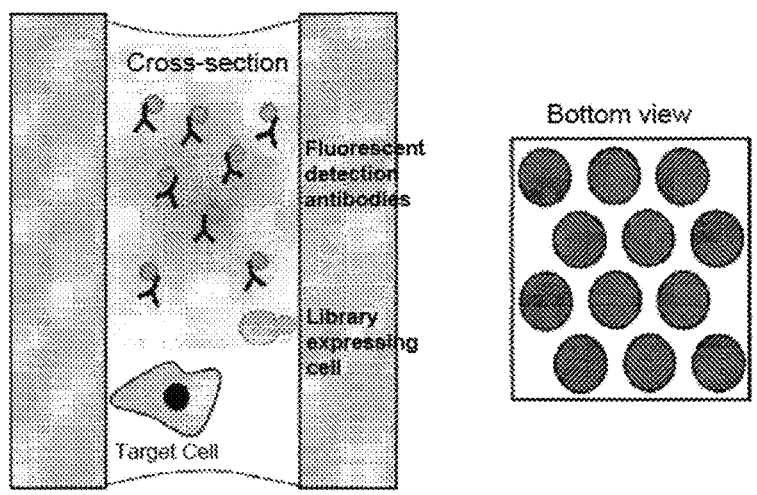
FIGS. 1A-1C schematically illustrate the steps of an exemplary microcapillary screening assay. The illustration on the left in each panel is a cross-sectional view from the side of a single microcapillary. The illustration on the right in each panel is a bottom view of a subsection of the array of microcapillaries. The shading in each case is intended to illustrate an electromagnetic signal, such as fluorescence.

Microcapillary arrays have recently been employed in approaches for high-throughput analysis and protein engineering with large numbers of biological samples, for example in an approach that has been termed "microcapillary single-cell analysis and laser extraction" or "µSCALE". See Chen et al. (2016) *Nature Chem. Biol.* 12:76-81; DOI: 10.1038/NCHEMBIO.1978. This approach relies on the spatial segregation of single cells within a microcapillary array, and thus enables repeated imaging, cell growth, and protein expression of the separate samples within each microcapillary of the microcapillary array. Accordingly, the technique enables massively parallel, quantitative biochemical and biophysical measurements on millions or multi-millions of samples within a microcapillary array, for example, in the analysis of millions or multi-millions of protein variants expressed from yeast, bacteria, or other suitable cells distributed throughout the array. Advantageously, the approach has allowed the simultaneous time-resolved kinetic analysis of the multiplexed samples, as well as the sorting of those cells based on targeted phenotypic features.

The development of µSCALE methods and apparatus for the quantitative biochemical and biophysical analysis of populations of biological variants has also been reported in U.S. Patent Application Publication No. 2016/0244749 A1, which is incorporated by reference herein in its entirety.

Extraction of the contents of a desired microcapillary according to the μSCALE approach requires, however, the inclusion of a radiation-absorbing material in each sample and the directing of electromagnetic radiation from a pulsed laser into this material, thus adding complexity to the extraction methods. In addition, earlier methods of screening of biological variants in arrays of microcavities relied on the addition of microparticles to the arrayed samples to partially or completely inhibit the transmission of electromagnetic radiation into and out of the sample in order to minimize signal emitted from microcavities lacking a desired binding activity. See U.S. Patent Application Publication No. U.S. 2014/0011690 A1. In some aspects of the instant disclosure, the screening methods do not rely on these additional sample components or manipulations, thus simplifying and improving the efficiency of the screening techniques. The screening methods have also been described in U.S. Patent Application No. 62/433,210 and Ser. No. 15/376,588, both filed on Dec. 12, 2016, the disclosures of which are incorporated herein by reference in their entireties.

In specific applications of these approaches, and as will be disclosed in more detail herein, the target molecule can be immobilized on a surface, such as the surface of a particle (e.g., a magnetic particle), a cell, or a microcapillary wall. The interaction between a variant protein and a target molecule in these approaches can then be measured by several methods, including methods utilizing detectable antibodies and methods of measuring detectable signals generated within the target cells. It will be understood that such methods can be used in high-throughput screens to discover protein variants that bind to target molecules, for example a target molecule on a cell or other surface.

Methods of Screening

Accordingly, in some aspects, the instant disclosure provides methods of screening a population of variant proteins comprising the steps of:
  providing a microcapillary array comprising a plurality of microcapillaries, each microcapillary comprising a variant protein, an immobilized target molecule, and a reporter element, wherein the variant protein associates with the immobilized target molecule with a particular affinity; and
  measuring a signal from at least one reporter element that indicates association of at least one variant protein with at least one immobilized target molecule to identify at least one microcapillary of interest.

In these methods, the microcapillary arrays preferably comprise a plurality of longitudinally fused capillaries, for example fused silica capillaries, although any other suitable material may be utilized in the arrays. See, e.g., PCT International Patent Publication Nos. WO2012/007537 and WO2014/008056, the disclosures of which are incorporated by reference herein in their entireties. Such arrays can be fabricated, for example, by bundling millions or billions of silica capillaries and fusing them together through a thermal process, although other suitable methods of fabrication may also be employed. The fusing process may comprise, for example, the steps of i) heating a capillary single draw glass that is drawn under tension into a single clad fiber; ii) creating a capillary multi draw single capillary from the single draw glass by bundling, heating, and drawing; iii) creating a capillary multi-multi draw multi capillary from the multi draw single capillary by additional bundling, heating, and drawing; iv) creating a block assembly of drawn glass from the multi-multi draw multi capillary by stacking in a pressing block; v) creating a block pressing block from the block assembly by treating with heat and pressure; and vi) creating a block forming block by cutting the block pressing block at a precise length (e.g., 1 mm).

In some embodiments, the fabrication method further comprises slicing the silica capillaries, thereby forming very high-density glass microcapillary arrays. In some embodiments, the microcapillary arrays may be cut to approximately 1 millimeter in height, but even shorter microcapillary arrays are contemplated, including arrays of 10 μm in height or even shorter. In some embodiments, even shorter microcapillary arrays are contemplated, including arrays of 1 μm, 2 μm, 3 μm, 4 μm, 5 μm, 6 μm, 7 μm, 8 μm, 9 μm, or 10 μm. In some embodiments, even longer microcapillary arrays are contemplated, including arrays of 10 mm or even longer. In some embodiments, of the arrays are 200 μm, 250 μm, 300 μm, 350 μm, 400 μm, 450 μm, 500 μm, 550 μm, 600 μm 650 μm, 700 μm, 750 μm, 800 μm, 850 μm, 900 μm, 950 μm, 1 mm, 2 mm, 3 mm, 4 mm, 5 mm, 6 mm, 7 mm, 8 mm, 9 mm, or 10 mm in height.

Such processes form very high-density microcapillary arrays that are suitable for use in the present methods. In an exemplary array, each microcapillary has an approximate 5 μm diameter and approximately 66% open space (i.e., representing the lumen of each microcapillary). In some arrays, the proportion of the array that is open ranges between about 50% and about 90%, for example about 60 to 75%, such as a microcapillary array provided by Hamamatsu that has an open area of about 67%. In one particular example, a 10×10 cm array having 5 μm diameter microcapillaries and approximately 66% open space has about 330 million total microcapillaries.

In various embodiments, the internal diameter of each microcapillary in the array ranges from between approximately 1 μm and 500 μm. In some arrays, each microcapillary can have an internal diameter in the range between approximately 1 μm and 300 μm; optionally between approximately 1 μm and 100 μm; further optionally between approximately 1 μm and 75 μm; still further optionally between approximately 1 μm and 50 μm; and still further optionally between approximately 5 μm and 50 μm.

In some microcapillary arrays, the open area of the array comprises up to 90% of the open area (OA), so that, when the pore diameter varies between 1 μm and 500 μm, the number of microcapillaries per cm of the array varies between approximately 460 and over 11 million. In some microcapillary arrays, the open area of the array comprises about 67% of the open area, so that, when the pore size varies between 1 μm and 500 μm, the number of microcapillaries per square cm of the array varies between approximately 340 and over 800,000. In some embodiments, the pore size is 1 μm, 5 μm, 10 μm 50 μm, 100 μm, 250 μm 350 or 500 μm. In some embodiments, the pore size is between 5 μm and 500 μm. In some embodiments, the pore size is between 10 μm and 450 μm. In some embodiments, the pore size is between 50 μm and 500 μm. In some embodiments, the pore size is between 100 μm and 500 μm. In some embodiments, the pore size is between 250 μm and 500 μm. In some embodiments, the pore size is between 350 μm and 500 μm. In some embodiments, the pore size is between 100 μm and 450 μm. In some embodiments, the pore size is between 250 μm and 450 μm. In some embodiments, the number of microcapillaries per square cm of the array is approximately 400; 500; 1000; 2,000; 3,000; 4,000; 5,000; 6,000; 7,000; 8,000; 9,000; 10,000; 20,000; 50,000; 100,000; 200,000; 300,000; 400,000; 500,000; 600,000; 700,000; or 800,000. In some embodiments, the number of microcapillaries per square cm of the array varies between approximately 500 and 800,000. In some embodiments, the number of microcapillaries per square cm of the array varies between approximately 1000 and 700,000. In some embodiments, the number of microcapillaries per square cm of the array varies between approximately 2000 and 600,000. In some embodiments, the number of microcapillaries per square cm of the array varies between approximately 10,000 and 800,000. In some embodiments, the number of microcapillaries per square cm of the array varies between approximately 10,000 and 700,000. In some embodiments, the number of microcapillaries per square cm of the array varies between approximately 50,000 and 800,000. In some embodiments, the number of microcapillaries per square cm of the array varies between approximately 50,000 and 700,000. In some embodiments, the number of microcapillaries per square cm of the array varies between approximately 100,000 and 700,000. In some embodiments, the number of microcapillaries per square cm of the array varies between approximately 100,000 and 600,000. In some embodiments, the number of microcapillaries per square cm of the array varies between approximately 100,000 and 500,000. In some embodiments, the number of microcapillaries per square cm of the array varies between approximately 500,000 and 800,000.

In one particular embodiment, a microcapillary array can be manufactured by bonding billions of silica capillaries and then fusing them together through a thermal process. After that slices (0.5 mm or more) are cut out to form a very high aspect ratio glass microcapillary array. Arrays are also commercially available, such as from Hamamatsu Photonics K. K. (Japan), Incom, Inc. (Massachusetts), Photonis Technologies, S.A.S. (France) Inc., and others. In some embodiments, the microcapillaries of the array are closed at one end with a solid substrate attached to the array.

The microcapillary arrays of the instant screening methods can comprise any number of microcapillaries within the array. In some embodiments, the microcapillary array comprises at least 100,000, at least 300,000, at least 1,000,000, at least 3,000,000, at least 10,000,000, or even more microcapillaries. The number of microcapillaries within an array is preferably chosen in view of the size of the variant protein library to be screened.

As described above, each capillary in the microcapillary arrays used in the instant screening methods comprises a variant protein, an immobilized target molecule, and a reporter element, where the variant protein is one of the population of variant proteins that is being subjected to the screening method. The population of variant proteins can be any population of proteins that can be suitably distributed within a microcapillary array. Ideally, the population of variant proteins is distributed in the microcapillary array so that each microcapillary comprises a small number of different variant proteins, preferably just a single different variant protein per microcapillary. Importantly, the population of variant proteins is chosen in combination with the immobilized target molecule, such that at least some of the proteins in the population can associate with the immobilized target molecule with a particular affinity, such that the association is detectable by measuring a signal from a reporter element. In some embodiments, the microcapillary screening methods of the instant invention allow for screening reactions and/or interactions (including binding interactions) that occur between the variant protein and the target molecule within minutes of the addition of the components to the microcapillary. In some embodiments, the reactions and/or interactions between the variant protein and the target molecule occur and/or are detectable within about 1 minute to about 10 minutes. In some embodiments, the reactions and/or interactions between the variant protein and the target molecule occur and/or are detectable within about 1 hour to about 6 hours. In some embodiments, the reactions and/or interactions between the variant protein and the target molecule occur and/or are detectable within a period of time such that the cells within the microcapillary are alive and healthy. In some embodiments, the reactions and/or interactions between the variant protein and the target molecule occur and/or are detectable within a period of time such that the cells within the microcapillary are viable. In some embodiments, the cells can be grown after removal from the microcapillary and/or microcavity. In some embodiments, the cells are viable after removal from the microcapillary and/or microcavity. In some embodiments, the reactions and/or interactions the between the variant protein and the target molecule occur within the microcapillary.

The term "protein", as used herein, refers both to full-length proteins or polypeptide sequences and to fragments thereof. Such fragments may include fragments that retain a functional activity, such as, for example, a binding activity. The terms "protein" and "polypeptide" are used interchangeably throughout the disclosure and include chains of amino acids covalently linked through peptide bonds, where each amino acid in the polypeptide may be referred to as an "amino acid residue". Use of the terms "protein" or "polypeptide" should not be considered limited to any particular length of polypeptide, e.g., any particular number of amino acid residues. The subject proteins may include proteins having non-peptidic modifications, such as post-translational modifications, including glycosylation, acetylation, phosphorylation, sulfation, or the like, or other chemical modifications, such as alkylation, acetylation, esterification, PEGylation, or the like. Additional modifications, such as the inclusion of non-natural amino acids within a polypeptide sequence or non-peptide bonds between amino acid residues should also be considered within the scope of the definition of the term "protein" or "polypeptide".

The population of variant proteins is preferably a population of proteins having minor variations, for example a population of proteins where each protein has a slightly different amino acid sequence. The screening assays can, therefore, identify variant protein sequences having desirable properties. Because the screens can be performed in such large numbers at microscopic scale, huge numbers of variant proteins can be assayed in relatively short times. In some embodiments, the screening process occurs within 4 hours to 6 hours. In some embodiments, the screening process occurs within 4 hours, 5 hours, or 6 hours. In some embodiments, the screening process requires between 1-3 seconds per microcapillary (i.e., cavity, microcapillary, microcavity, pore, and/or micropore). In some embodiments, the screening process requires about 1 second per microcapillary (i.e., cavity, microcapillary, microcavity, pore, and/or micropore). In some embodiments, the screening process requires about 2 seconds per microcapillary (i.e., cavity, microcapillary, microcavity, pore, and/or micropore). In some embodiments, the screening process requires about 3 seconds per microcapillary (i.e., cavity, microcapillary, microcavity, pore, and/or micropore).

In some embodiments, each microcapillary in the microcapillary array comprises 0 to 5 different variant proteins from the population of variant proteins. In specific embodiments, each microcapillary in the microcapillary array comprises 0 to 4, 0 to 3, 0 to 2, or even 0 to 1 different variant proteins from the population of variant proteins. It should be understood that the different variant proteins in the population of variant proteins differ in their molecular structure, whether the difference is in their amino acid sequence or in some other chemical modification of the protein.

It should be understood that each microcapillary will typically comprise many multiple copies of the same variant protein, depending on the source and expression level of the particular variant protein (see below). In some embodiments, each microcapillary will comprise thousands, tens of thousands, hundreds of thousands, millions, billions, or even more molecules of a particular variant protein, depending on how the variant protein is delivered to or expressed within the microcapillary.

The population of variant proteins is typically generated using a genetic library in a biological expression system, for example in an in vitro (i.e., cell-free) expression system or in an in vivo or cellular expression system. Exemplary cellular expression systems include, for example, animal systems (e.g., mammalian systems), fungal systems (e.g., yeast systems), bacterial systems, insect systems, or plant systems. In specific embodiments, the expression system is a mammalian system or a yeast system. The expression system, whether cellular or cell-free, typically comprises a library of genetic material encoding the population of variant proteins. Cellular expression systems offer the advantage that cells with a desirable phenotype, for example cells that express a particular variant protein of interest, such as a variant protein capable of associating with an immobilized target molecule with high affinity, can be grown and multiplied, thus facilitating and simplifying the identification and characterization of the proteins of interest expressed by the cells.

Genetic libraries encoding large populations of variant proteins are well known in the art of bioengineering. Such libraries are often utilized in systems relying on the process of directed evolution to identify proteins with advantageous properties, such as high-affinity binding to target molecules, stability, high expression, or particular spectroscopic, e.g., fluorescence, or enzymatic activities. Often the libraries include genetic fusions with sequences from the host expression system, for example fragments of proteins directing subcellular localization, where the expressed population of variant fusion proteins are directed by the targeting fragment to a particular location of the cell or virus particle for purposes of activity screening of the variant protein population. Large numbers of variant proteins (e.g., $10^6$ variants, $10^8$ variants, $10^{10}$ variants, $10^{12}$ variants, or even more variants) can be generated using routine bioengineering techniques, as is well known in the art. Such libraries can include any of the variant proteins described herein, including antibodies, antibody fragments, single chain variable fragments, or natural protein ligands.

Accordingly, in some embodiments, the variant proteins are soluble proteins, for example soluble proteins that are secreted by a cellular expression system. Exemplary soluble variant proteins include antibodies and antibody fragments, alternative protein scaffolds, such as disulfide-bonded peptide scaffolds, extracellular domains of cell-surface receptor proteins, receptor ligands, such as, for example, G-protein coupled receptor ligands, other peptide hormones, lectins, and the like. Advantageously, the variant proteins screened for binding activity in the instant methods do not need to be covalently attached to the cell or virus that expresses them in order to be identified following a screening assay, since a variant protein with a desired binding activity and the cell that expressed it remain co-localized within the same microcapillary throughout the assay. Isolation of the contents of the desired microcapillary, followed by propagation of the cell or virus clone responsible for expression of the desired variant protein, thereby enables the identification and characterization of that protein. Unlike screening assays where a variant protein of interest is displayed by fusion of the protein to a molecule on the surface of a cell or virus particle, the variant proteins identified in the instant screening methods need not be altered in any way following their identification. The observed activities of the variant proteins in the screens are thus more likely to represent the actual activities of those proteins in their subsequent applications.

In other embodiments, however, it may be desirable for the variant proteins to be membrane-associated proteins, for example proteins remaining associated with the surface of a cell or a viral particle in an expression system. Screening of cell-associated variant proteins may be desirable where the variant protein and its target molecule mediate interactions between two cells within a biological tissue. The ability to screen against cell-associated variant proteins may also be desirable in screening for interactions with traditionally "non-druggable" protein targets, such as, for example, G-protein coupled receptors or ion channels.

In addition to a variant protein, each microcapillary in the microcapillary arrays of the instant screening methods also comprises an immobilized target molecule. The immobilized target molecule serves as the potential binding partner for the variant protein of the screening assay. Unlike the population of variant proteins, where each microcapillary ideally contains a variant protein of slightly different sequence, the immobilized target molecules ideally have the same molecular structure in each microcapillary of the array.

In some embodiments, the target molecule is a target protein or polypeptide, a target nucleic acid, a target carbohydrate, a target lipid, or a combination of two or more of these target molecules. For example, in some embodiments the target molecule can be a lipid-modified or glycosylated protein. In some embodiments, the target molecule is immobilized on a surface. In more specific embodiments, the target molecule is immobilized on the surface of a cell, such as a target cell, the surface of a bead, the surface of a microcapillary wall, or another suitable surface. In other more specific embodiments, the target molecule is a native protein, for example a native protein immobilized on the surface of a cell. In still other more specific embodiments, the target molecule is immobilized on a surface configured to settle in the microcapillary by gravitational sedimentation.

As previously noted, in the methods of the instant disclosure, the variant protein associates with the immobilized target molecule with a particular affinity within a microcapillary. Importantly, such affinities should be sufficiently strong for variant proteins of interest that the association can be measured by a signal from a reporter element. Binding affinities are typically assessed by a dissociation constant ($K_d$), as is well understood by those of ordinary skill in the art, where the lower the dissociation constant, the higher the affinity. In some embodiments, the association between the variant protein of interest and the immobilized target molecule displays a dissociation constant in the millimolar to micromolar range. In specific embodiments, the association displays a dissociation constant from micromolar to high nanomolar (i.e., $10^{-6}$ M to $10^{-8}$ M). In more specific embodiments, the association displays a dissociation constant from lower nanomolar to high picomolar (i.e., $10^{-8}$ M to $10^{-10}$ M). In even more specific embodiments, the association displays a dissociation constant in the picomolar range (i.e., $10^{-10}$ M to $10^{-12}$ M), or even lower. In some embodiments, a first cell expresses and secretes the variant protein or polypeptide and a second cell comprises the target, such that the first cells binds to the second cell. In some embodiments, the second cell expresses the target. In some embodiments, the second cell is labeled with the target. In some embodiments, the first cell binds to the second cell in the microcapillary. In some embodiments, the first cell binds to the second cell in the microcapillary and/or microcavity.

In some embodiments, the target molecule is a target protein or polypeptide, a target nucleic acid, a target carbohydrate, a target lipid, or a combination of two or more of these target molecules. For example, in some embodiments the target molecule can be a lipid-modified or glycosylated protein. In some embodiments, the target molecule is immobilized on a surface. In more specific embodiments, the target molecule is immobilized on the surface of a cell, such as a target cell, the surface of a bead, the surface of a microcapillary wall, or another suitable surface. In other more specific embodiments, the target molecule is a native protein, for example a native protein immobilized on the surface of a cell. In still other more specific embodiments, the target molecule is immobilized on a surface configured to settle in the microcapillary by gravitational sedimentation. In some embodiments, one, two, three, or four, or more target molecules are employed, in order to identify variants that bind to one, two, three, or four, or more target molecules. In some embodiments, the target molecules are contained separately in separate and different microcapillaries. In some embodiments, the target molecules are contained separately in separate and different microcapillaries within a single array. In some embodiments, the target molecules are contained separately in separate and different microcapillaries within one or more arrays. In some embodiments, the target molecules are contained together in a single microcapillary. In some embodiments, the target molecules are contained together in a single microcapillary within a single array. In some embodiments, the one, two, three, or four, or more target molecules to which the variant binds are derivatives or variants of an original target molecule, including chemical modifications, secondary post-translational modifications, or sequence identity variants (including, for example, variants with 70%, 75%, 80%, 85%, 90%, 95%, or 99% sequence identity to an original nucleic acid or amino acid target sequence).

In addition to a variant protein and an immobilized target molecule, each microcapillary in the microcapillary array of the instant screening methods also comprises a reporter element. Importantly, the reporter element provides a measureable signal indicative of the association of a variant protein with an immobilized target molecule and thus serves to identify a microcapillary containing variant proteins of interest.

In some embodiments, the reporter element is a labeled antibody or other molecule capable of binding to each variant protein in the population of variant proteins. More specifically, the reporter element is a fluorescently-labeled antibody or other binding molecule.

In some embodiments, the labeled antibody is a labeled primary antibody or a labeled secondary antibody. For purposes of this disclosure, a primary antibody is typically considered to be an antibody that binds directly to an antigen of interest, whereas a secondary antibody is typically considered to be an antibody that binds to a constant region on a primary antibody for purposes of labeling the primary antibody. Accordingly, secondary antibodies are frequently labeled with fluorophores or other detectable labels or are labeled with enzymes that are capable of generating detectable signals. They are generally specific for a primary antibody from a different species. For example, a goat or other animal species may be used to generate secondary antibodies against a mouse, chicken, rabbit, or nearly any primary antibody other than an antibody from that animal species, as is understood by those of ordinary skill in the art. In specific embodiments, the labeled antibody is a fluorescent antibody or an enzyme-linked antibody. In some embodiments, the fluorophore can include but is not limited to AlexaFluor 3, AlexaFluor 5, AlexaFluor 350, AlexaFluor 405, AlexaFluor 430, AlexaFluor 488, AlexaFluor 500, AlexaFluor 514, AlexaFluor 532, AlexaFluor 546, AlexaFluor 555, AlexaFluor 568, AlexaFluor 594, AlexaFluor 610, AlexaFluor 633, AlexaFluor 647, AlexaFluor 660, AlexaFluor 680, AlexaFluor 700, and AlexaFluor 750 (Molecular Probes AlexaFluor dyes, available from Life Technologies, Inc. (USA)). In some embodiments, the fluorophore can include but is not limited to Cy dyes, including Cy2, Cy3, Cy3B, Cy3.5, Cy5, Cy5.5 and Cy7 (available from GE Life Sciences or Lumiprobes). In some embodiments the fluorophore can include but is not limited to DyLight 350, DyLight 405, DyLight 488, DyLight 550, DyLight 594, DyLight 633, DyLight 650, DyLight 680, DyLight 750 and DyLight 800 (available from Thermo Scientific (USA)). In some embodiments, the fluorophore can include but is not limited to a FluoProbes 390, FluoProbes 488, FluoProbes 532, FluoProbes 547H, FluoProbes 594, FluoProbes 647H, FluoProbes 682, FluoProbes 752 and FluoProbes 782, AMCA, DEAC (7-Diethylaminocoumarin-3-carboxylic acid); 7-Hydroxy-4-methylcoumarin-3; 7-Hydroxycoumarin-3; MCA (7-Methoxycoumarin-4-acetic acid); 7-Methoxycoumarin-3; AMF (4'-(Aminomethyl)fluorescein); 5-DTAF (5-(4,6-Dichlorotriazinyl)aminofluorescein); 6-DTAF (6-(4,6-Dichlorotriazinyl)aminofluorescein); 6-FAM (6-Carboxyfluorescein), 5(6)-FAM cadaverine; 5-FAM cadaverine; 5(6)-FAM ethylenediamme; 5-FAM ethylenediamme; 5-FITC (FITC Isomer I; fluorescein-5-isothiocyanate); 5-FITC cadaverin; Fluorescein-5-maleimide; 5-IAF (5-Iodoacetamidofluorescein); 6-JOE (6-Carboxy-4',5'-dichloro-2',7'-dimethoxyfluorescein); 5-CRI 10 (5-Carboxyrhodamine 110); 6-CRI 10 (6-Carboxyrhodamine 110); 5-CR6G (5-Carboxyrhodamine 6G); 6-CR6G (6-Carboxyrhodamine 6G); 5(6)-Carboxyrhodamine 6G cadaverine; 5(6)-Caroxyrhodamine 6G ethylenediamme; 5-ROX (5-Carboxy-X-rhodamine); 6-ROX (6-Carboxy-X-rhodamine); 5-TAMRA (5-Carboxytetramethylrhodamine); 6-TAMRA (6-Carboxytetramethylrhodamine); 5-TAMRA cadaverine; 6-TAMRA cadaverine; 5-TAMRA ethylenediamme; 6-TAMRA ethylenediamme; 5-TMR C6 maleimide; 6-TMR C6 maleimide; TR C2 maleimide; TR cadaverine; 5-TRITC; G isomer (Tetramethylrhodamine-5-isothiocyanate); 6-TRITC; R isomer (Tetramethylrhodamine-6-isothiocyanate); Dansyl cadaverine (5-Dimethylaminonaphthalene-1-(N-(5-aminopentyl))sulfonamide); EDANS C2 maleimide; fluorescamine; NBD; and pyrromethene and derivatives thereof. In some embodiments, the reporter element used can be a donkey anti-goat IgG secondary antibody labeled with AlexaFluor 633.

Figure 1B:
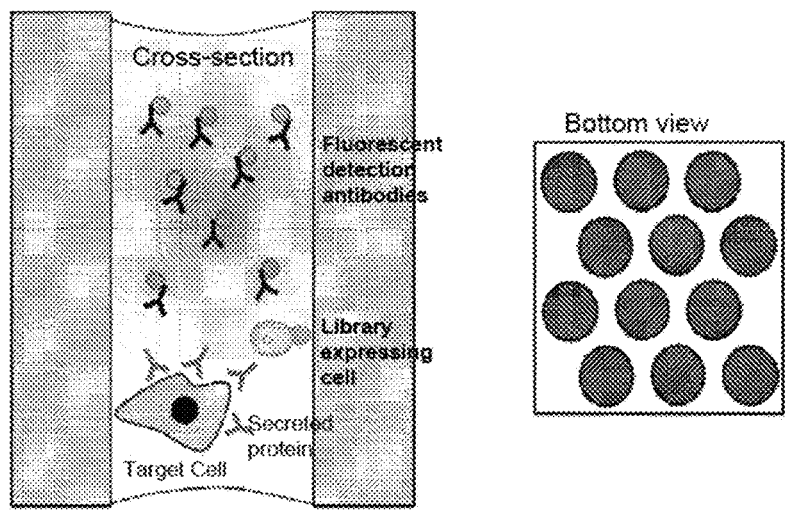
Figure 1C:
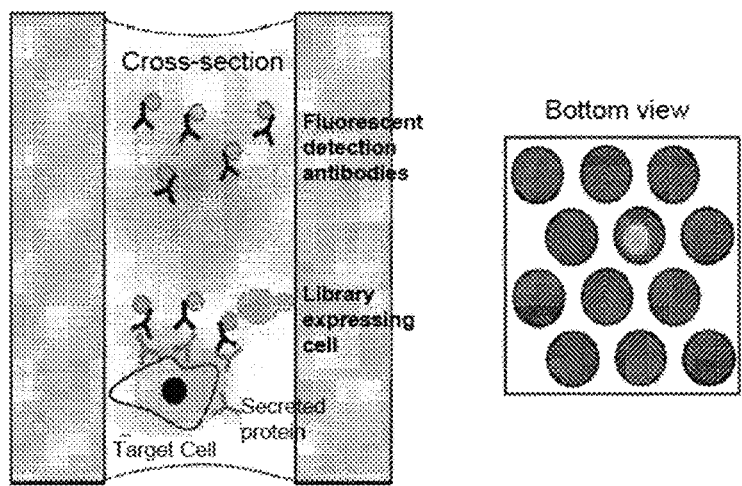

In some of the method embodiments, for example in the screening methods illustrated in FIGS. 1A-1C, the variant protein mediates the association of a reporter element with a target molecule, in this example, a target molecule on the surface of a target cell. As shown in FIG. 1B, where the variant protein (here designated as a "secreted protein") has sufficient affinity for its target molecule on the target cell that the variant proteins associate with the target cell under the conditions of the microcapillary solution. The reporter element (here designated as "fluorescent detection antibodies") binds to the variant protein, ideally at an epitope that does not affect the affinity of the variant protein for the target molecule, as shown in FIG. 1C.

As would be understood by those of ordinary skill in the art, when a soluble reporter element, such as a fluorescent antibody, is used in the instant screening methods, the signal emitted by any excess reporter element remaining free in solution (i.e., either not bound to a variant protein or bound to a variant protein that is not bound to a target molecule) within the microcapillary should not be so high that it overwhelms the signal of reporter elements associated with a target molecule via a variant protein (see, e.g., the unassociated fluorescent detection antibodies illustrated in FIG. 1C). Such background signals can be minimized, however, by limiting the concentration of labeled antibody or other reporter element within the microcapillary solution. In addition, where signals from the screening methods are measured using a fluorescent microscope, configuring the microscope to image a relatively narrow depth of field bracketing the location of the target molecules (e.g., the bottom of the microcapillaries when target cells have settled there by gravitational sedimentation) can minimize the background signal from reporter elements not associated with the target molecule.

In other embodiments, the reporter element is an intracellular reporter element that generates a detectable signal in connection with a binding event, such as, for example, the association of a variant protein with an immobilized target molecule, for example, a receptor or other target molecule on the surface of the cell. In these embodiments, the reporter element may comprise an entire cellular pathway, such as, for example, an intracellular signaling pathway. Such a pathway should include, or be engineered to include, a detectable signal as the downstream readout of the pathway. In contrast to the assays illustrated in FIGS. 1A-1C, where the detectable signal is bound to the outer surface of the target cell, the detectable signal in these embodiments would typically be generated inside the target cell.

Many intracellular signaling pathways have been developed for use in high throughput screening assays, in particular in drug discovery screens, and can be adapted for use in the instant assays. See, e.g., Michelini et al. (2010) *Anal. Bioanal. Chem.* 398:227-38. In particular, any cellular assay where a binding event with a target molecule on the surface of a cell results in the generation of a measurable signal, in particular a fluorescent signal, can be used as a reporter element in the instant assays. Preferably, the cells can be engineered to express a target molecule of interest on their surface, so that the binding of a particular variant protein to the target molecule and the consequent activation of the intracellular signaling pathway result in the production of a detectable signal from the reporter element, thus enabling the identification of the microcapillary as a positive hit. The expression of a green fluorescent protein (GFP), or any of a wide variety of variant fluorescent proteins, is often used as a readout in such cellular assays and can serve as the reporter element endpoint in the instant methods. Reporter elements can also include RFP (red fluorescent protein) as well as YFP (yellow fluorescent protein), and variants thereof. Alternatively, the signaling readout can be provided by luciferase or other related enzymes that produce bioluminescent signals, as is well understood by those of ordinary skill in the art. See, e.g., Kelkar et al. (2012) *Curr. Opin. Pharmacol.* 12:592-600. Other well-known enzymatic reporters from bacterial and plant systems include β-galactosidase, chloramphenicol acetyltransferase, β-glucuronidase (GUS), and the like, which can be adapted for use in the instant screening assays with suitable colorogenic substrates. Transcriptional reporters using firefly luciferase and GFP have been used extensively to study the function and regulation of transcription factors. They can likewise be adapted for use in the instant screening assays. Exemplary intracellular signaling systems are available commercially, for example the Cignal™ Reporter Assay kits from Qiagen (see, e.g., www.sabiosciences.com/reporterassays.php), which are available with either luciferase or GFP readouts. Such systems can be suitably re-engineered for use in the instant screening methods.

It should be understood that a variant protein expression system, in particular where the expression system is a cellular expression system, can be combined with the immobilized target molecule and the reporter element (or suitable components, such as cellular components, responsible for generating the immobilized target molecule and/or reporter element) prior to the expression of the variant proteins and/or prior to delivery of an assay mixture into the array of microcapillaries. Such approaches advantageously allow for flexibility and control in the timing of interactions between the components compared to prior art microcapillary screening systems, where all of the components of the screening assays are typically mixed and loaded into the microcapillaries in static form. In contrast, the instant methods enable some or all of the components of a binding assay to be generated in situ within the microcapillaries, either by allowing for the growth of cellular components, the expression of genetic components, or both.

It should also be understood that the concentrations of each component of the screening assay within a microcapillary, including the concentration of the variant protein, the concentration of the immobilized target molecule, and the concentration of the reporter element, can be modulated as desired in an assay in order to achieve an optimal outcome. In particular, it may be desirable to modulate the concentration of variant protein and/or immobilized target molecule to achieve the desired level of association between these components. The level of association will also depend on the particular affinity between these components, wherein a higher affinity results in a higher level of association for a given concentration of the components, and a lower affinity results in a lower level of association of the components for a given concentration. Concentration of the reporter element may likewise be modulated in order to achieve optimum levels of signal output, as would be understood by those of ordinary skill in the art. In some embodiments, the reporter element employed includes a secondary antibody, including those commercially available. In some embodiments the dilution range is 1:200-1:2000. In some embodiments the dilution range is 1:300-1:2000. In some embodiments the dilution range is 1:300-1:1500. In some embodiments the dilution range is 1:400-1:1500. In some embodiments the dilution range is 1:500-1:1500. In some embodiments the dilution range is 1:200-1:1000. In some embodiments the dilution range is 1:500-1:1000. In some embodiments the dilution range is 1:1000-1:2000. In some embodiments the dilution range is 1:1500-1:2000. In some embodiments, the dilution is 1:200, 1:300, 1:400, 1:500, 1:600, 1:700, 1:800, 1:900, 1:1000, 1:1500, or 1:2000. In some embodiments, the fluorophore can include but is not limited to AlexaFluor 3, AlexaFluor 5, AlexaFluor 350, AlexaFluor 405, AlexaFluor 430, AlexaFluor 488, AlexaFluor 500, AlexaFluor 514, AlexaFluor 532, AlexaFluor 546, AlexaFluor 555, AlexaFluor 568, AlexaFluor 594, AlexaFluor 610, AlexaFluor 633, AlexaFluor 647, AlexaFluor 660, AlexaFluor 680, AlexaFluor 700, and AlexaFluor 750 (Molecular Probes AlexaFluor dyes, available from Life Technologies, Inc. (USA)). In some embodiments, the fluorophore can include but is not limited to Cy dyes, including Cy2, Cy3, Cy3B, Cy3.5, Cy5, Cy5.5 and Cy7 (available from GE Life Sciences or Lumiprobes). In some embodiments the fluorophore can include but is not limited to DyLight 350, DyLight 405, DyLight 488, DyLight 550, DyLight 594, DyLight 633, DyLight 650, DyLight 680, DyLight 750 and DyLight 800 (available from Thermo Scientific (USA)). In some embodiments, the fluorophore can include but is not limited to a FluoProbes 390, FluoProbes 488, FluoProbes 532, FluoProbes 547H, FluoProbes 594, FluoProbes 647H, FluoProbes 682, FluoProbes 752 and FluoProbes 782, AMCA, DEAC (7-Diethylaminocoumarin-3-carboxylic acid); 7-Hydroxy-4-methylcoumarin-3; 7-Hydroxycoumarin-3; MCA (7-Methoxycoumarin-4-acetic acid); 7-Methoxycoumarin-3; AMF (4'-(Aminomethyl)fluorescein); 5-DTAF (5-(4,6-Dichlorotriazinyl)aminofluorescein); 6-DTAF (6-(4,6-Dichlorotriazinyl)aminofluorescein); 6-FAM (6-Carboxyfluorescein), 5(6)-FAM cadaverine; 5-FAM cadaverine; 5(6)-FAM ethylenediamme; 5-FAM ethylenediamme; 5-FITC (FITC Isomer I; fluorescein-5-isothiocyanate); 5-FITC cadaverin; Fluorescein-5-maleimide; 5-IAF (5-Iodoacetamidofluorescein); 6-JOE (6-Carboxy-4', 5'-dichloro-2',7'-dimethoxyfluorescein); 5-CRI 10 (5-Carboxyrhodamine 110); 6-CRI 10 (6-Carboxyrhodamine 110); 5-CR6G (5-Carboxyrhodamine 6G); 6-CR6G (6-Carboxyrhodamine 6G); 5(6)-Carboxyrhodamine 6G cadaverine; 5(6)-Caroxyrhodamine 6G ethylenediamme; 5-ROX (5-Carboxy-X-rhodamine); 6-ROX (6-Carboxy-X-rhodamine); 5-TAMRA (5-Carboxytetramethylrhodamine); 6-TAMRA (6-Carboxytetramethylrhodamine); 5-TAMRA cadaverine; 6-TAMRA cadaverine; 5-TAMRA ethylenediamme; 6-TAMRA ethylenediamme; 5-TMR C6 maleimide; 6-TMR C6 maleimide; TR C2 maleimide; TR cadaverine; 5-TRITC; G isomer (Tetramethylrhodamine-5-isothiocyanate); 6-TRITC; R isomer (Tetramethylrhodamine-6-isothiocyanate); Dansyl cadaverine (5-Dimethylaminonaphthalene-1-(N-(5-aminopentyl))sulfonamide); EDANS C2 maleimide; fluorescamine; NBD; and pyrromethene and derivatives thereof. In some embodiments, the reporter element used can be a donkey anti-goat IgG secondary antibody labeled with AlexaFluor 633.

In some embodiments, each microcapillary in the microcapillary arrays of the instant screening methods further comprises an agent or agents to improve viability of the cellular expression system. Specifically, the agent or agents is included to prevent cell damage during the step of isolating the contents of the microcapillary of interest, for example by a laser pulse (see below). In preferred embodiments, the agent is methylcellulose (for example at 0.001 to 10 wt %), dextran (for example at 0.5 to 10 wt %), pluronic F-68 (for example at 0.01 to 10 wt %), polyethylene glycol ("PEG") (for example at 0.01 to 10 wt %), polyvinyl alcohol ("PVA") (for example at 0.01 to 10 wt %), or the like. Alternatively, or in addition, each microcapillary in the microcapillary arrays of the instant screening methods can further comprise a growth additive, such as, for example, 50% conditioned growth media, 25% standard growth media, or 25% serum. In some embodiments, the conditioned growth media is conditioned for 24 hours. In some embodiments, the added agent is insulin, transferrin, ethanolamine, selenium, an insulin-like growth factor, or a combination of these agents or any of the agents recited above.

The screening methods of the instant disclosure preferably include the further step of measuring a signal from at least one reporter element that indicates association of at least one variant protein with at least one immobilized target molecule to identify at least one microcapillary of interest. In some embodiments, the signal measured is a fluorescent signal, an absorbance signal, a bright-field signal, a dark-field signal, a phase contrast signal, or the like. Accordingly, the measuring step can be performed by an appropriate detector device, for example a device capable of detecting electromagnetic radiation or any other suitable signal. In specific embodiments, the measuring step is performed by a microscope, such as a fluorescence microscope or any other microscope configured to detect the above-mentioned signals.

It should be understood that in preferred embodiments, the microcapillaries utilized in the instant screening methods do not comprise microparticles capable of inhibiting the transmission of electromagnetic radiation. In other words, the microcapillaries are preferably fully transparent to electromagnetic radiation incident on the microcapillary array, in particular along the longitudinal axes of the microcapillaries. In other preferred embodiments, the microcapillaries of the instant screening methods do not comprise magnetic microparticles or beads. In still other preferred embodiments, the microcapillaries of the instant screening methods do not comprise microparticles capable of inhibiting the transmission of electromagnetic radiation, magnetic microparticles, or magnetic beads.

In other preferred embodiments, the microcapillaries utilized in the instant screening methods do not comprise an electromagnetic radiation absorbent material. It should be understood, however, that the component of a reporter element responsible generating a measurable signal in the screening method, for example the fluorophore on a fluorescent antibody, should not be considered an electromagnetic radiation absorbent material for purposes of this aspect of the invention.

In some embodiments, the instant screening methods further comprise the step of isolating the contents of the microcapillary of interest. In specific embodiments, the contents of the microcapillary of interest are isolated by pulsing the microcapillary of interest with a laser. In some embodiments, the laser is a diode laser. In some embodiments, the laser is a nanosecond pulsed laser. In some embodiments, the laser is a picosecond pulsed laser. More specifically, the laser can be a diode laser or a diode-pumped Q-switched Nd:YLF laser. In some embodiments, the laser can be directed at the water-glass interface between the microcapillary wall and the sample contained in the microcapillary. Without intending to be bound by theory, it is believed that firing a UV laser at this interface can break the meniscus/water surface tension that normally holds a sample in the microcapillary, thus allowing the sample to fall out of the array via the force of gravity. In other embodiments, the contents of the microcapillary of interest are isolated by laser-triggered vapor force expansion. In some embodiments, the contents of the microcapillary are isolated by breaking the glass of the microcapillary itself.

Systems for Screening and Sample Recovery

According to another aspect of the invention are provided systems for screening a population of variant proteins comprising:

an array comprising a plurality of microcapillaries, each microcapillary comprising a variant protein, an immobilized target molecule, and a reporter element, wherein the variant protein associates with the immobilized target molecule with a particular affinity. The components of these screening devices are described in detail above.

In some embodiments, the screening systems further comprise an optical source and a detector. In some embodiments, the optical source is a Nikon Intensilight Illuminator. In some embodiments, the optical detector is an imaging camera such as a charge-coupled device (CCD) or a complementary metal-oxide-semiconductor (CMOS) imaging sensor. In some embodiments, the optical detector is a Hamamatsu ORCA-Flash4.0 CMOS camera. The optical source and detector are chosen according to the particular reporter element used in the screening system. For example, where the reporter element generates a fluorescent signal, the optical source provides excitation light of an appropriate wavelength to excite the fluorescent probe. Likewise, the detector is chosen to be sensitive to the wavelength of light emitted by the fluorescent probe. The optical source and the detector may, for example, be components of a microscope, such as a fluorescent microscope, or they may be separate devices, as would be understood by those of ordinary skill in the art. Preferably, the fluorescent microscope is an inverted fluorescent microscope.

Figure 6A:
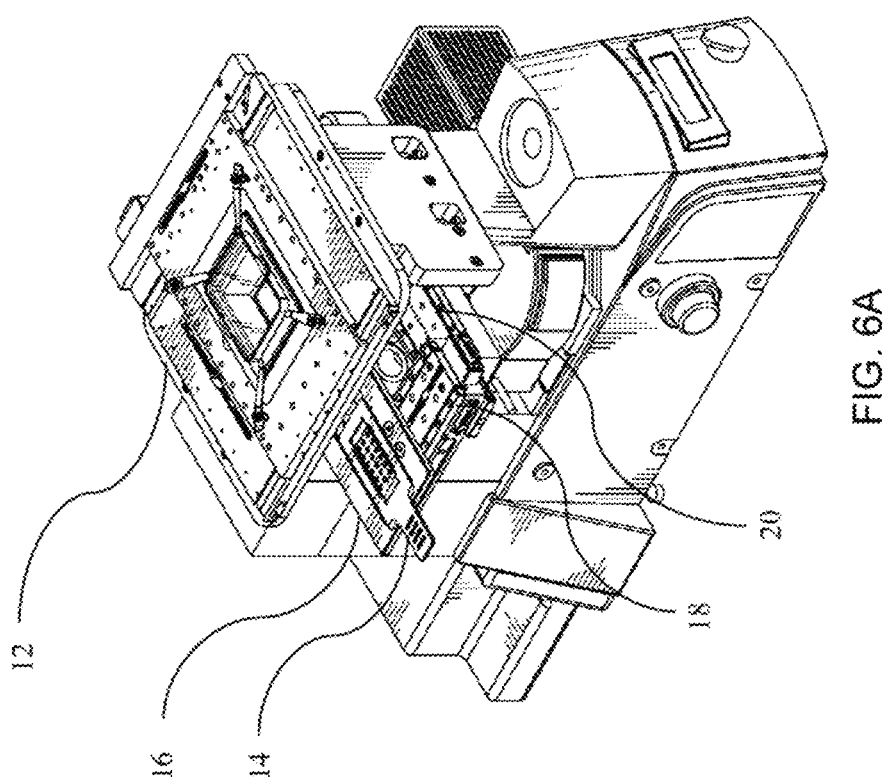
FIGS. 6A-6E are different views of a microscope system designed to carry out the screening methods of the instant disclosure.
Figure 6B:
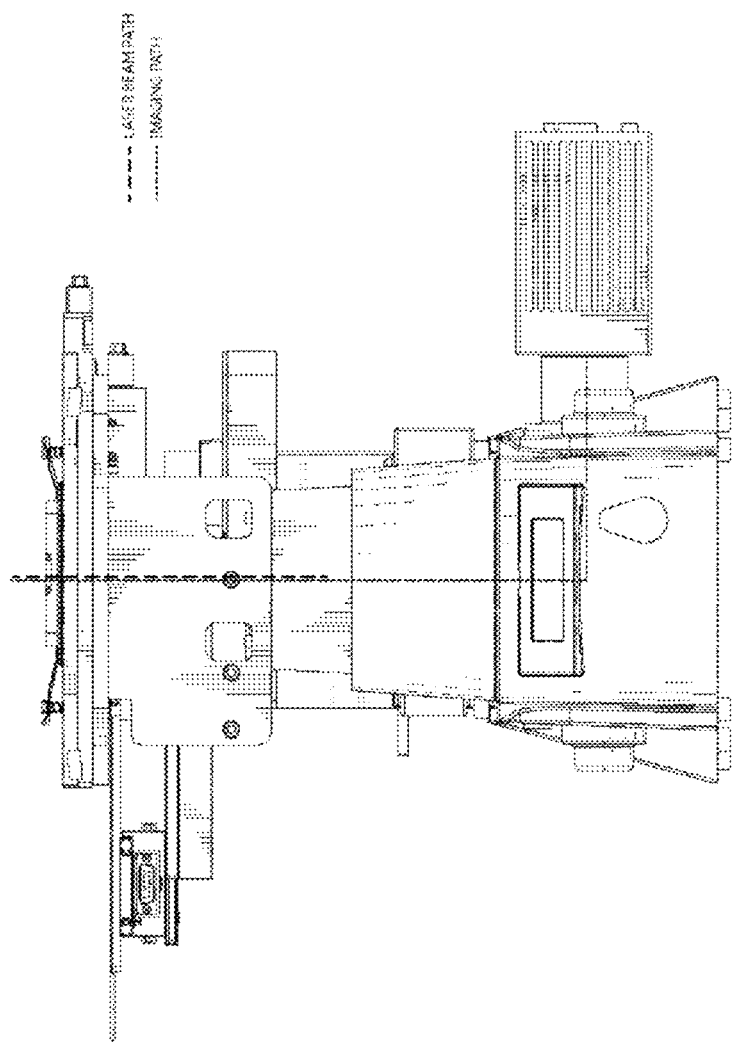
Figure 6C:
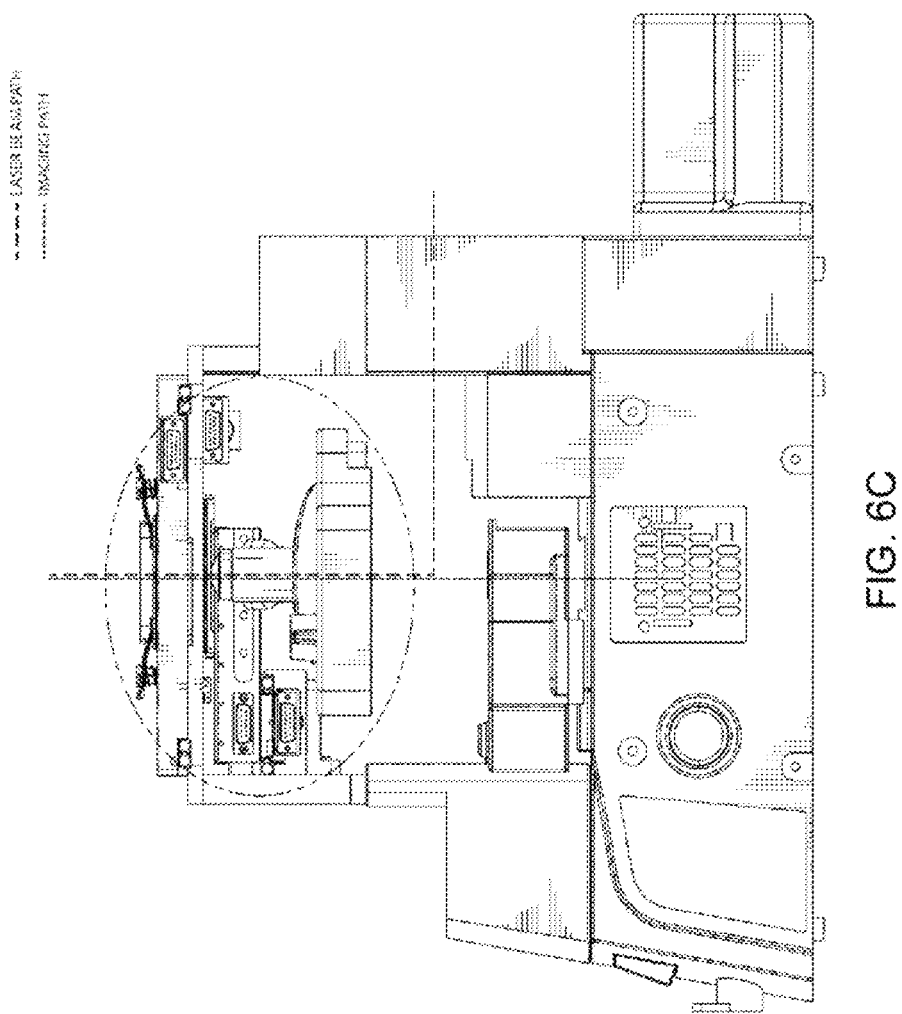
Figure 6D:
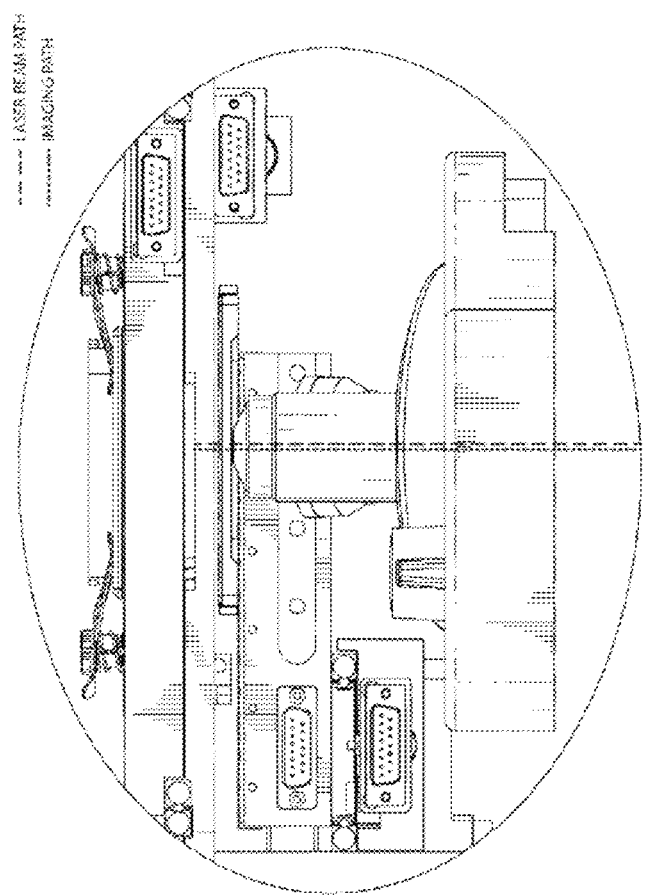
Figure 6E:
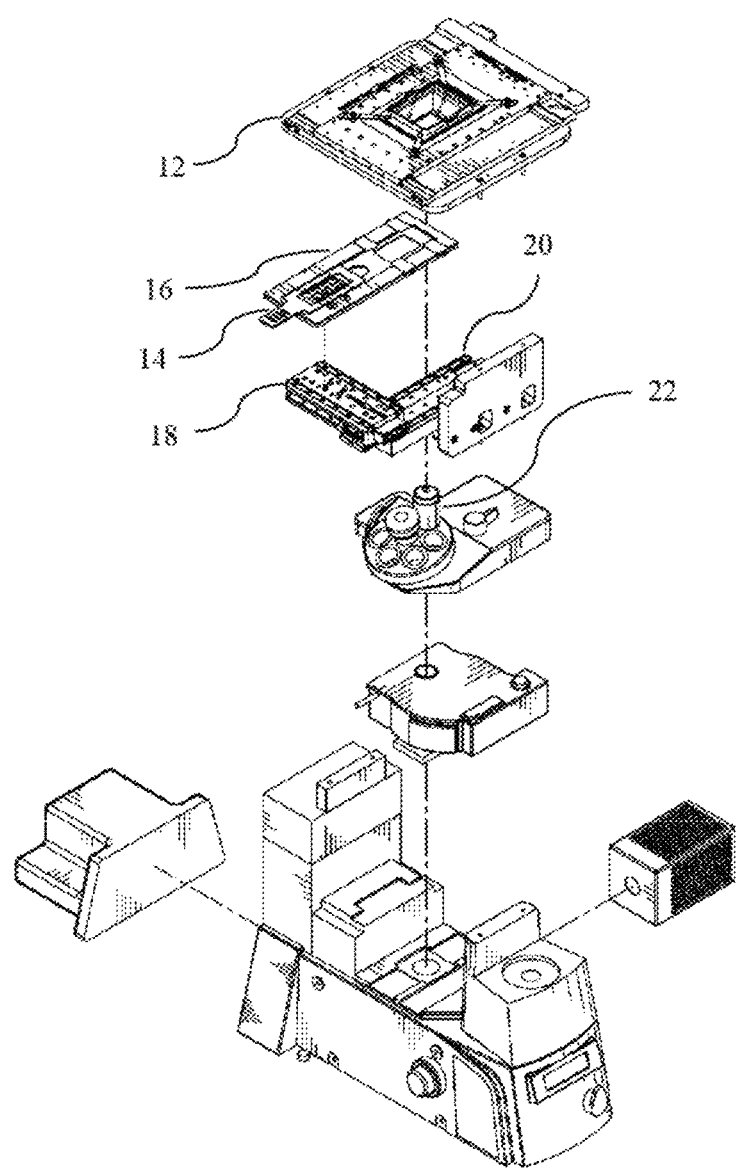

An exemplary microscope for screening populations of variant proteins according to the instant methods and recovering samples of interest from the screens is illustrated in the drawings of FIGS. 6A-6E. FIG. 6A shows a perspective view from above the microscope, illustrating the screening array stage 12, the recovery array 14, the recovery array holder 16, the first recovery array stage 18, and the second recovery array stage 20. FIG. 6B shows a front view of the device. FIG. 6C shows a view from the right side. A magnified view of the right side of the device is provided in FIG. 6D, which illustrates in detail the relationship between the screening array stage, the recovery array stages, and the recovery array in this system. FIG. 6E provides an exploded view of various components of this particular multi-stage sample recovery system.

In some aspects, the disclosure thus provides multi-stage sample recovery systems comprising:
 a screening array stage, wherein the screening array stage is controllable in two dimensions relative to a microscope objective and is configured for reversible association with a screening array; and
 a first recovery array stage, wherein the first recovery array stage is controllable in at least one dimension relative to the microscope objective and is configured for reversible association with a recovery array;
 wherein the screening array stage and the first recovery array stage are controllable independently of one another. In some embodiments, the screening array stage and first recovery stage are physically separate from one another. In some embodiments, the screening array stage that is controllable in two dimensions is controllable in a horizontal dimension and/or a vertical dimension relative to the microscope objective. In some embodiments, the first recovery array stage that is controllable in at least one dimension is controllable in a horizontal dimension and/or a vertical dimension relative to the microscope objective. In some embodiments, the first recovery array stage that is controllable in at least one dimension is controllable in a horizontal dimension relative to the microscope objective. In some embodiments, the first recovery array stage that is controllable in at least one dimension is controllable in a vertical dimension relative to the microscope objective. In some embodiments, the screening array stage can be positioned closer to the first recovery stage in the vertical dimension. In some embodiments, the screening array stage can be positioned further away from the recovery stage in the vertical dimension. In some embodiments, the screening array stage and first recovery stage can be moved and/or repositioned during the sample recovery process. In some embodiments, the screening array stage can be moved and/or repositioned during the sample recovery process. In some embodiments, the first recovery stage can be moved and/or repositioned during the sample recovery process. In some embodiments, the screening array stage and first recovery stage can be moved and/or repositioned in both the horizontal dimension and the vertical dimension during the sample recovery process. In some embodiments, the screening array stage and first recovery stage can be moved and/or repositioned in the horizontal dimension during the sample recovery process. In some embodiments, the screening array stage and first recovery stage can be moved and/or repositioned in the vertical dimension during the sample recovery process. In some embodiments, the sample moves from the screening array stage and into the first recovery stage during the sample recovery process. In some embodiments, the sample is collected from the screening array stage and into the first recovery stage during the sample recovery process. In some embodiments, the sample moves from the screening array stage and into the first recovery stage during the sample recovery process and this movement is facilitated by the movement and/or repositioning of the screening array stage and/or the first recovery stage. In some embodiments, the sample moves from the screening array stage and into the first recovery stage during the sample recovery process and this movement is facilitated by the movement and/or repositioning of the screening array stage. In some embodiments, the sample moves from the screening array stage and into the first recovery stage during the sample recovery process and this movement is facilitated by the movement and/or repositioning of the first recovery stage. In some embodiments, the sample is collected from the screening array stage and into the first recovery stage during the sample recovery process and this collection is facilitated by the movement and/or repositioning of the screening array stage and/or the first recovery stage.

In some embodiments, the sample is collected from the screening array stage and into the first recovery stage during the sample recovery process and this collection is facilitated by the movement and/or repositioning of the screening array stage. In some embodiments, the sample is collected from the screening array stage and into the first recovery stage during the sample recovery process and this collection is facilitated by the movement and/or repositioning of the first recovery stage. In some embodiments, the screening array stage can be moved and/or repositioned in the horizontal dimension and/or vertical dimension during the sample recovery process. In some embodiments, the screening array stage can be moved and/or repositioned in the horizontal dimension during the sample recovery process. In some embodiments, the screening array stage can be moved and/or repositioned in the vertical dimension during the sample recovery process. In some embodiments, the first recovery stage can be moved and/or repositioned in the horizontal dimension and/or vertical dimension during the sample recovery process. In some embodiments, the first recovery stage can be moved and/or repositioned in the horizontal dimension during the sample recovery process. In some embodiments, the first recovery stage can be moved and/or repositioned in the vertical dimension during the sample recovery process. In some embodiments, the laser is in a fixed position. In some embodiments, the laser is in a fixed position relative to the microscope objective. In some embodiments, the laser passes through the screening array stage before passing through the first recovery stage. In some embodiments, the laser passes through the screening array stage before passing through the first recovery stage, causing the sample to move from the screening array stage and into the first recovery stage. In some embodiments, the laser passes through (e.g., activated and fires through) the screening array stage first, causing the sample to move from the screening array stage and into the first recovery stage. In some embodiments, the sample is moved from the screening array stage and into the first recovery stage by the laser. In some embodiments, the laser passes through one capillary (i.e., cavity, microcapillary, microcavity, pore, and/or micropore) in the screening array stage and into one capillary (i.e., cavity, microcapillary, microcavity, pore, and/or micropore) in the first recovery stage. In some embodiments, the laser passes through one capillary (i.e., cavity, microcapillary, microcavity, pore, and/or micropore) in the screening array stage and into one capillary (i.e., cavity, microcapillary, microcavity, pore, and/or micropore) in the first recovery stage, causing the sample to move from the one capillary (i.e., cavity, microcapillary, microcavity, pore, and/or micropore) in the screening array stage and into the one capillary (i.e., cavity, microcapillary, microcavity, pore, and/or micropore) in the first recovery stage. In some embodiments, the laser remains in a fixed position (i.e., does not move relative to the microscope objective). In some embodiments, the screening array stage and first recovery stage can be moved and/or repositioned in the horizontal dimension and/or vertical dimension during the sample recovery process while the laser remains in a fixed position (i.e., does not move relative to the microscope objective). In some embodiments, the screening array stage and first recovery stage can be moved and/or repositioned in the horizontal dimension during the sample recovery process while the laser remains in a fixed position (i.e., does not move relative to the microscope objective). In some embodiments, the screening array stage and first recovery stage can be moved and/or repositioned in the vertical dimension during the sample recovery process while the laser remains in a fixed position (i.e., does not move relative to the microscope objective). In some embodiments, the screening array stage can be moved and/or repositioned in the horizontal dimension and/or vertical dimension during the sample recovery process while the laser remains in a fixed position (i.e., does not move relative to the microscope objective). In some embodiments, the screening array stage can be moved and/or repositioned in the horizontal dimension during the sample recovery process while the laser remains in a fixed position (i.e., does not move relative to the microscope objective). In some embodiments, the screening array stage can be moved and/or repositioned in the vertical dimension during the sample recovery process while the laser remains in a fixed position (i.e., does not move relative to the microscope objective). In some embodiments, the first recovery stage can be moved and/or repositioned in the horizontal dimension and/or vertical dimension during the sample recovery process while the laser remains in a fixed position (i.e., does not move relative to the microscope objective). In some embodiments, the first recovery stage can be moved and/or repositioned in the horizontal dimension during the sample recovery process while the laser remains in a fixed position (i.e., does not move relative to the microscope objective). In some embodiments, the first recovery stage can be moved and/or repositioned in the vertical dimension during the sample recovery process while the laser remains in a fixed position (i.e., does not move relative to the microscope objective). In some embodiments, the vertical distance between the two stages is about 20 mm. In some embodiments, the vertical distance between the screening stage and the recovery stage is about 20 mm. In some embodiments, there is a gap between the screening array which is located (e.g., sits recessed) in the screening stage and the recovery slide which is located (e.g., sits recessed) in the recovery stage. In some embodiments, the gap between the screening array which sits recessed and/or is located in the screening stage and the recovery slide which sits recessed and/or is located in the recovery stage is about 1 mm, about 2 mm, or about 3 mm. In some embodiments, the gap between the screening array which sits recessed and/or is located in the screening stage and the recovery slide which sits recessed and/or is located in the recovery stage is about 1 mm. In some embodiments, the gap between the screening array which sits recessed and/or is located in the screening stage and the recovery slide which sits recessed and/or is located in the recovery stage is about 2 mm. In some embodiments, the gap between the screening array which sits recessed and/or is located in the screening stage and the recovery slide which sits recessed and/or is located in the recovery stage is about 3 mm. In some embodiments, the recovery slide is referred to as a first recovery array. In some embodiments, the gap between the screening array which sits recessed and/or is located in the screening stage and the first recovery array which sits recessed and/or is located in the recovery stage is about 1 mm, about 2 mm, or about 3 mm. In some embodiments, the gap between the screening array which sits recessed and/or is located in the screening stage and the first recovery array which sits recessed and/or is located in the recovery stage is about 1 mm. In some embodiments, the gap between the screening array which sits recessed and/or is located in the screening stage and the first recovery array which sits recessed and/or is located in the recovery stage is about 2 mm. In some embodiments, the gap between the screening array which sits recessed and/or is located in the screening stage and the first recovery array which sits recessed and/or is located in the recovery stage is about 3 mm. In some embodiments, the screening array stage and the recovery stage are positioned so that the microscope objective can image both the screening array and the recovery slide. In some embodiments, the screening array stage and the first recovery array stage are positioned so that the microscope objective can image both the screening array and the first recovery array. In some embodiments, and the screening array is within the working distance of the objective. In some embodiments, and the first recovery array is within the working distance of the objective. In some embodiments, the screening array and the first recovery array are within the working distance of the objective. In some embodiments, and the screening array stage is within the working distance of the objective. In some embodiments, and the first recovery array stage is within the working distance of the objective. In some embodiments, the screening array stage and the first recovery array stage are within the working distance of the objective. The working distance is typically the distance over which the microscope objective is capable of imaging (i.e., the working distance of the objective is the gap or distance between front lens of objective and the sample). In some embodiments, the working distance of the microscope objective is about 1 mm to about 30 mm. In some embodiments, the working distance of the microscope objective is about 5 mm to about 25 mm. In some embodiments, the working distance of the microscope objective is about 10 mm to about 25 mm. In some embodiments, the working distance of the microscope objective is about 10 mm to about 20 mm. In some embodiments, the travel distance for the microscope employed with the present methods is about 1 mm to about 30 mm. In some embodiments, the travel distance for the microscope employed with the present methods is about 5 mm to about 25 mm. The travel distance is generally the distance the Z axis of the microscope can travel. In some embodiments, the travel distance for the microscope employed with the present methods is about 10 mm to about 25 mm. In some embodiments, the travel distance for the microscope employed with the present methods is about 10 mm to about 20 mm. In some embodiments, the recovery array is a first recovery array. In some embodiments, the recovery array is a second recovery array. In some embodiments, the microcapillary array is within the working distance. In some embodiments, the microcapillary array is within the working distance of the projective or objective so that the microcapillary array can be focused on. In some embodiments, the microscope system has the ability to focus on both the microcapillary array and the recovery array and/or recovery slide. In some embodiments, both the screening array and the recovery array and/or recovery slide are within the travel distance of the objective. In some embodiments, the screening array is within the travel distance of the objective. In some embodiments, the recovery array and/or recovery slide is within the travel distance of the objective. In some embodiments, both the screening array and the recovery array and/or recovery slide are within the travel distance of the objective so that the screening array and the recovery array and/or recovery slide can be focused on. See, as exemplary embodiments, the figures provided herewith, including FIGS. 6A-6E, as discussed in the next paragraph as well as throughout the application.

As mentioned above, various views of an exemplary sample recovery system are provided in FIGS. 6A-6E. In particular, FIG. 6E illustrates the relative positioning of a screening array stage 12, a recovery array 14, a recovery array holder 16, a first recovery array stage 18, a second recovery array stage 20, and a microscope objective 22. The optical pathways of an extraction beam, in this case a laser beam, and of the screening array image, are illustrated from the three perspectives shown in FIGS. 6B-6D as "laser beam path" and "imaging path", respectively. The screening array stage is preferably configured to accommodate an array of microscale sample vessels, in particular within an aperture that allows for the transmission of the optical beams through the associated array. Such a stage is shown in more detail in FIG. 7A. An exemplary recovery array stage is illustrated in FIG. 7B. At least one recovery array stage is preferably connected to a recovery array holder, for example as illustrated in FIG. 6E, to facilitate the reversible association of the recovery array with the recovery array stage. Reversible association refers to the ability of the recovery array to be able to associate and dissociate with the recovery array stage (e.g., a first recovery stage) before, during, or after the sample recovery process. In some embodiments, reversible indicates that the recovery array can be placed into the system and/or removed from the system, in some cases more than once. In some embodiments, the recovery array is reversibly associated with the recovery array stage via spring tension, gravity, magnetic forces, friction, screws/fasteners, and/or Velcro.

In preferred embodiments, the multi-stage sample recovery system further comprises a screening array reversibly associated with the screening array stage. Reversible association refers to the ability of the screening array to be able to associate and dissociate with the screening array stage before, during, or after the sample recovery process. In some embodiments, reversible indicates that the screening array can be placed into the system and/or removed from the system, in some cases more than once. In some embodiments, the screening array is reversibly associated with the screening array stage via spring tension, gravity, magnetic forces, friction, screws/fasteners, and/or Velcro. Such screening arrays typically comprise a plurality of microscale sample vessels, preferably a plurality of microcapillaries as described in more detail above, although other screening arrays could suitably be utilized in the instant systems, as would be understood by those of ordinary skill in the art.

In other preferred embodiments, the instant multi-stage sample recovery system further comprises a recovery array reversibly associated with the first recovery array stage. More specifically, the recovery array comprises a recovery vessel or a plurality of recovery vessels. Such recovery vessels, for example as illustrated in recovery array 14 of FIGS. 6A and 6E, can in some embodiments be configured to prevent cell damage and/or to promote cell growth. For example, each recovery vessel within a recovery array can comprise an agent or agents to prevent cell damage. In some embodiments the agent is methylcellulose (for example at 0.001 to 10 wt %), dextran (for example at 0.5 to 10 wt %), pluronic F-68 (for example at 0.01 to 10 wt %), polyethylene glycol ("PEG") (for example at 0.01 to 10 wt %), polyvinyl alcohol ("PVA") (for example at 0.01 to 10 wt %), or the like. Alternatively, or in addition, each recovery vessel can comprise a growth additive, such as, for example, 50% conditioned growth media, 25% standard growth media, 25% serum, or another suitable growth additive. See also U.S. Patent Application No. 62/433,210 and Ser. No. 15/376,588, both filed on Dec. 12, 2016. In some embodiments, the conditioned growth media is conditioned for 24 hours. In some embodiments, the added agent is insulin, transferrin, ethanolamine, selenium, an insulin-like growth factor, or a combination of these agents or any of the agents recited above. Configuration of a recovery vessel to promote cell growth is well understood by those of ordinary skill in the art of cell culture.

In some embodiments, the recovery vessels can be configured for an amplification reaction, such a polymerase chain reaction or a reverse-transcription polymerase chain reaction, or for a sequencing reaction, such as a DNA sequencing reaction. Configuration of a recovery vessel for an amplification reaction, a sequencing reaction, or any other such analytical reaction useful in identifying or characterizing samples recovered from a screening array using the instant sample recovery systems is well understood by those of ordinary skill in the analytical arts.

In preferred embodiments, the multi-stage sample recovery systems comprise both a screening array reversibly associated with the screening array stage and a recovery array reversibly associated with the first recovery array stage. More specifically, the screening array comprises a plurality of microscale sample vessels, and the recovery array comprises a plurality of recovery vessels.

As previously noted, the instant multi-stage sample recovery systems typically comprise an optical source and an optical detector to identify samples of interest within a screening array. In some cases, for example where a bioluminescent signal is being monitored, a separate optical source may not be required, and the systems may comprise only an optical detector. In either case, the optical detector is typically configured to monitor optical signals emitted from samples in a screening array by optically coupling the screening array to the detector through an aperture in the screening array stage. As described above, observation of optical signals from reporter elements within the sample vessels of the screening array enables the identification of specific sample vessels holding samples of interest, and the contents of those sample vessels can then be recovered by a pulse from the extraction beam generator. The optical detector, for example an imaging camera such as a charge-coupled device (CCD) or a complementary metal-oxide-semiconductor (CMOS) imaging sensor, is ideally capable of imaging large numbers of sample vessels from the screening array within a single field. In some embodiments, the optical detector is a charge-coupled device (CCD). In some embodiments, the optical detector is complementary metal-oxide-semiconductor (CMOS) imaging sensor. In some embodiments, the optical detector is a photodiode. Where fluorescent labels are used in the reporter elements, imaging detectors are typically chosen for their sensitivity in the visible range of the electromagnetic spectrum. Fluorescence emission from the screening array is directed to the optical detector, typically through a microscope objective, via the imaging path of the system. Commercial microscopes, such as, for example, Nikon Eclipse series inverted microscopes and the like, can be suitably adapted for use in the instant systems, as would be understood by those of ordinary skill in the art.

In some embodiments, the multi-stage sample recovery systems further comprise an extraction beam generator optically coupled through an aperture in the screening array stage to one microscale sample vessel within the screening array. More specifically, the extraction beam can be a laser beam, for example a beam emitted by a diode laser, a diode-pumped Q-switched laser, such as a diode-pumped Q-switched Nd:YLF laser, or another appropriate laser device. In some embodiments, the laser is a diode laser. In some embodiments, the laser is a nanosecond pulsed laser. In some embodiments, the laser is a picosecond pulsed laser. Where the system comprises an array of microcapillaries, the extraction beam can be directed at the water-glass interface between the microcapillary wall and the sample contained in the microcapillary. Use of lasers to isolate the contents of specific microcapillaries identified by fluorescence imaging within an array of microcapillaries has been described previously. See, e.g., Chen et al. (2016) *Nature Chem. Biol.* 12:76-81; DOI: 10.1038/NCHEMBIO.1978 and U.S. Patent Application Publication No. 2016/0244749 A1.

In preferred embodiments, the extraction beam is directed from below the targeted microscale sample vessel. It should also be understood, however, that the extraction beam can alternatively be directed from above the targeted microscale sample vessel if so desired.

In specific embodiments, the system further comprises a second recovery array stage. In more specific embodiments, the second recovery array stage is positioned orthogonally to the first recovery array stage. According to these embodiments, samples can be recovered automatically from a screening array into a recovery array having recovery vessels arranged in orderly grids, in particular grids with x rows and y columns, where x and y can independently be 3, 10, 30, 100, or even more.

In some embodiments, the screening array stage and the recovery array stage or stages are controllable by one or more electronic motors as would be understood by those of ordinary skill in the art.

In some embodiments, the screening array and the recovery array of the instant systems are configured so that at least one microscale sample vessel and at least one recovery vessel are positioned within a working distance of the microscope objective. In some embodiments, the working distance, including the vertical distance, is from about 0.1 mm to 40 mm. In some embodiments, the working distance, including the vertical distance, is from about 1 mm to 40 mm. In some embodiments, the working distance, including the vertical distance, is from about 2 mm to 30 mm. In some embodiments, the working distance, including the vertical distance, is from about 1.5 mm to 30 mm. In some embodiments, the working distance, including the vertical distance, is from about 2.5 mm to 30 mm. In some embodiments, the working distance, including the vertical distance, is from about 2 mm to 25 mm. In some embodiments, the working distance, including the vertical distance, is from about 3 mm to 30 mm. In some embodiments, the working distance, including the vertical distance, is from about 3 mm to 25 mm. More specifically, the working distance is from about 2.5 mm to about 25 mm. In these embodiments, the systems allow for the simultaneous imaging of the contents of a microscale sample vessel of interest and the associated recovery vessel. In more specific embodiments, the working distance of the microscope objective is from about 4 mm to about 10 mm or even from about 6 mm to about 8 mm, for example about 7.4 mm. In some embodiments, the recovery array is a first recovery array. In some embodiments, the recovery array is a second recovery array.

As previously noted, in preferred embodiments the screening arrays of the instant multi-stage sample recovery systems comprise a plurality of microcapillaries. More specifically, the screening arrays comprise at least 100,000, at least 300,000, at least 1,000,000, at least 3,000,000, at least 10,000,000, or even more microcapillaries. In some embodiments, the array comprises at least 100,000, at least 200,000, at least 300,000, at least 400,000, at least 500,000, at least 600,000, at least 700,000, at least 800,000, at least 1,000,000, at least 1,500,000, at least 2,000,000, at least 2,500,000, or at least 3,000,000 or more microcapillaries.

As also previously noted, in preferred embodiments the recovery arrays of the instant multi-stage sample recovery systems comprise one or more recovery vessels. Accordingly, in such systems, the recovery arrays may comprise at least 1 recovery vessel, at least 3 recovery vessels, at least 10 recovery vessels, at least 30 recovery vessels, at least 100 recovery vessels, or even more recovery vessels.

In preferred embodiments, the recovery array of the instant systems is positioned below the screening array. In some embodiments, the recovery array and the screening array are at least 25 mm, at least 30 mm, at least 35 mm, at least 40 mm, at least 45 mm, or at least 50 mm or more apart. In some embodiments, the recovery array and the screening array are at least 30 mm, at least 35 mm, or at least 40 mm apart. In some embodiments, the recovery array and the screening array are at least at least 35 mm or at least 40 mm apart. In some embodiments, the recovery array and the screening array are at least at least 35 mm apart. In some embodiments, the recovery array is at least 25 mm, at least 30 mm, at least 35 mm, at least 40 mm, at least 45 mm, or at least 50 mm below the screening array. In some embodiments, the recovery array is at least 30 mm, at least 35 mm, or at least 40 mm below the screening array. In some embodiments, the recovery array is at least 35 mm or at least 40 mm below the screening array. In some embodiments, the recovery array is at least 35 mm below the screening array.

It will be readily apparent to one of ordinary skill in the relevant arts that other suitable modifications and adaptations to the methods and applications described herein can be made without departing from the scope of the invention or any embodiment thereof. Having now described the present invention in detail, the same will be more clearly understood by reference to the following Examples, which are included herewith for purposes of illustration only and are not intended to be limiting of the invention.

EXAMPLES

Example 1. Screening for a Secreted EGFR-Binding Protein

FIG. 1A-FIG. 1C illustrate an exemplary screening method for a soluble protein capable of associating with a cell-surface protein (e.g., the epidermal growth factor receptor ("EGFR")) as the immobilized target molecule, in this case an immobilized target protein. FIG. 1A (left panel) shows the target cell, which expresses EGFR on its surface. Also shown is a "library expressing cell", which expresses a population of variant proteins, and a number "fluorescent detection antibodies" in the microcapillary solution. A bottom view of the microcapillary array is illustrated in the right panel.

Components of Each Microcapillary According to this Screening Assay:
1. Cells secreting the variant protein of interest (the "library expressing cell"). The variant protein of interest is preferably a member of a population of variant proteins, i.e., a protein library.
2. Target protein immobilized on a surface of a "target cell". In this example, the target protein is a native, cell-surface receptor (i.e., EGFR). Alternatively, however, the target protein could be immobilized on another surface, such as a bead surface or a surface of the microcapillary itself
3. Reporter element
   a. In this example, the reporter element corresponds to a fluorescently-labeled antibody specific for the secreted protein (i.e., the "fluorescent detection antibodies"). The antibody specifically localizes to an epitope on the secreted protein but ideally does not interfere with the binding of the secreted protein to the target protein on the target cell.
   b. Alternatively, the reporter element can be a signaling pathway within the cells that express the target protein. If a secreted variant protein binds the target protein on the cell surface and activates the signaling pathway within the target cell, the binding interaction will generate a fluorescent signal within the cell (not shown).
4. Reaction buffer:
   a. Can be media for the library-expressing cells or for the target cells.
   b. Can be a mammalian imaging solution.

Illustration of Method:
Step 1: Add all components into microcapillary (see FIG. 1A).
Step 2: A specific "secreted protein" is expressed by the library-expressing cell into the microcapillary. Secreted protein variants capable of binding to the target protein are localized to the target cell surface as shown (see FIG. 1B).
Step 3: Fluorescent detection antibodies associated with the bound secreted protein variants are observed in association with target cells in specific microcapillaries (see FIG. 1C).

Detailed Description and Sample Data:
To demonstrate this method, a yeast vector library expressing a protein designed to bind to EGFR on human cancer cells was created. In this library, some yeast variants were capable of expressing the protein, while other variants were not able to express the protein. Yeast cells, cancer cells, and a fluorescent antibody against the expressed protein were added to the microcapillary. After 18 hours, the microcapillary array was imaged. Further details and results of the screen are provided in Example 3 below.

Example 2. Hybridoma Screening Against Mammalian Cells

General Background
Current methods to screen binding interactions between proteins or other target molecules typically rely on the use of "display" methods, e.g., phage display, bacterial display, yeast display, mammalian display, or virus display. In the display methods, a library of genes encoding protein variants is expressed at the surface of the cell or phage. The protein variants are incubated with a soluble version of the target molecule in order to identify protein variants capable of binding to the target. The library can be screened by panning or by fluorescence-activated cell sorting ("FACS"). Such assays have two primary limitations: 1) the engineered protein is typically tethered to the display platform; and 2) it is usually advantageous for a soluble form of the target molecule to exist. Therefore, it can be difficult to develop reliable assays for variant proteins that bind to many target molecules, in particular membrane proteins, such as G-protein coupled receptors and other such receptors.

Hybridoma Screening Against Mammalian Cells
To identify antibody variants with specific binding to a target molecule, hybridomas (which secrete antibody variants) were added to a cancer cell line that expresses high levels of EGFR as the target molecule. Labeled antibodies specific for the secreted antibodies were then added.

Materials:
Cells:
  Mouse hybridoma
  A431 target cells (human cancer cell line expressing high levels of EGFR)
Detection Antibodies:
  Anti-mouse secondary antibody labeled with Alexa488 (a fluorophore)
Media for Cell Culture:
  DMEM-10% fetal bovine serum
  DMEM-10% horse serum Cell line growth and preparation. Mouse hybridoma cells were cultured in complete media (Dulbecco's Modified Eagle's Medium with 10% horse serum). The hybridoma cells were washed twice with PBSA and suspended in complete media at 600 cells/µL. The A431 cells were cultured in complete media (Dulbecco's Modified Eagle's Medium with 10% fetal bovine serum). The A431 cells were washed twice with PBSA and stained with a LiveGreen fluorescent signal. The A431 cells were then suspended in the complete media containing hybridoma at a final concentration of 1800 cells/uL.

Assay setup. Following mixing of the two cell types, detection antibodies were added to the reaction mixture: 1:100 dilution of secondary (anti-mouse Alexa488). This reaction mixture was then loaded into an ethanol-sterilized, corona-treated microcapillary array (40 μm diameter, 1 mm thick). A 2 mm slab of 1% weight/volume agarose was placed on the array to help prevent evaporation. After each hour, the sample was imaged under fluorescence and bright-field microscopy.

Figure 2A:
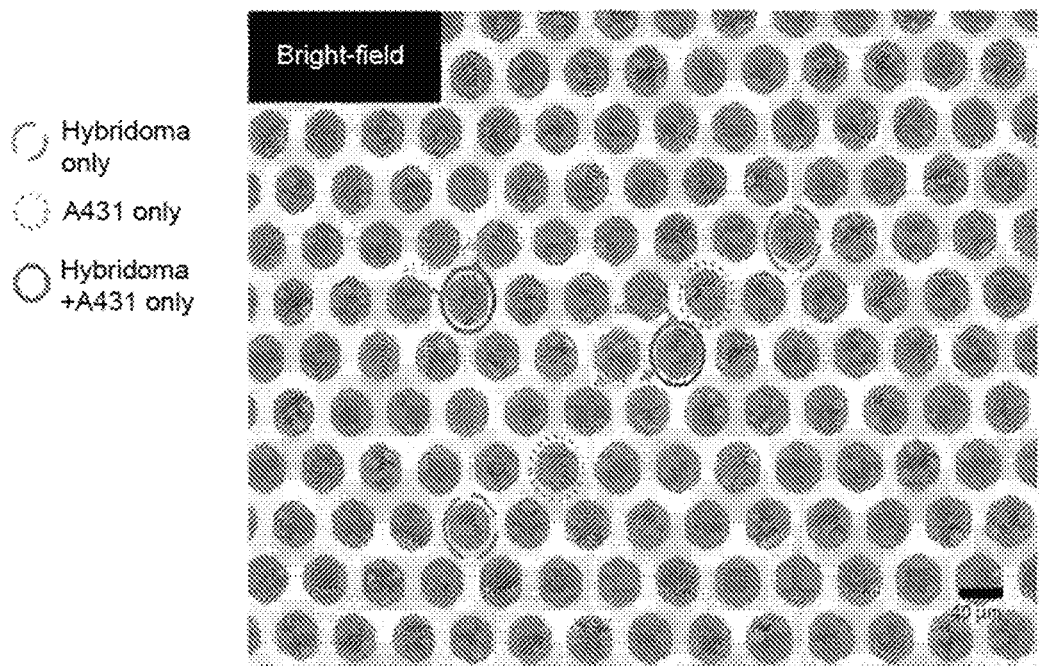
FIGS. 2A-C show the bottom view of a subsection of a microcapillary array illustrating hybridoma screening against mammalian cells, where the cells are imaged using either bright-field (FIG. 2A), LiveGreen (FIG. 2B), or a fluorescent anti-mouse secondary antibody (FIG. 2C).
Figure 2B:
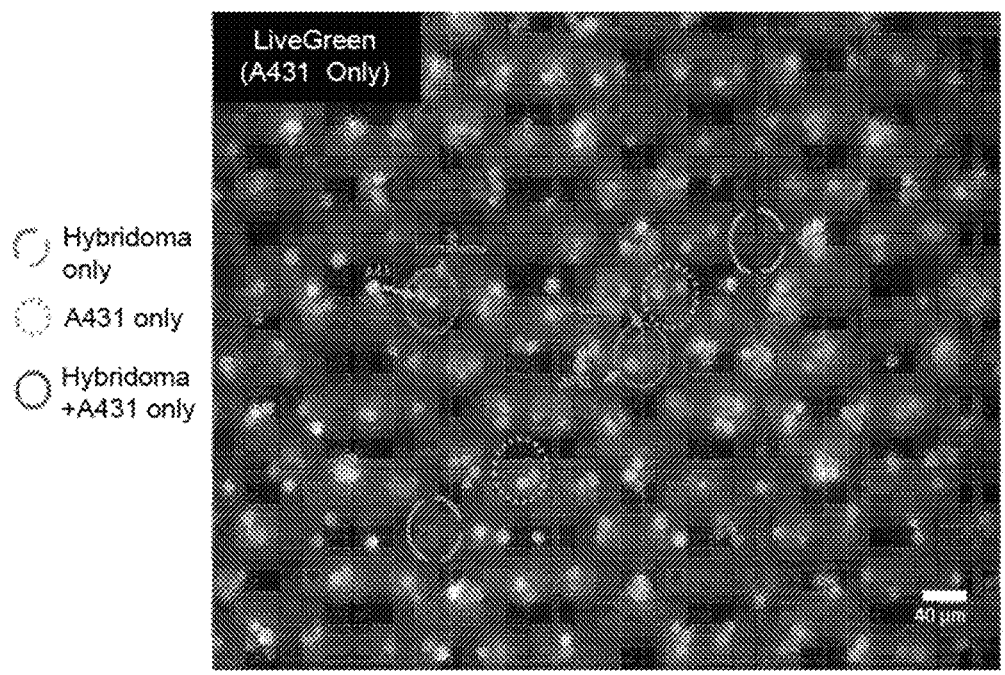
Figure 2C:
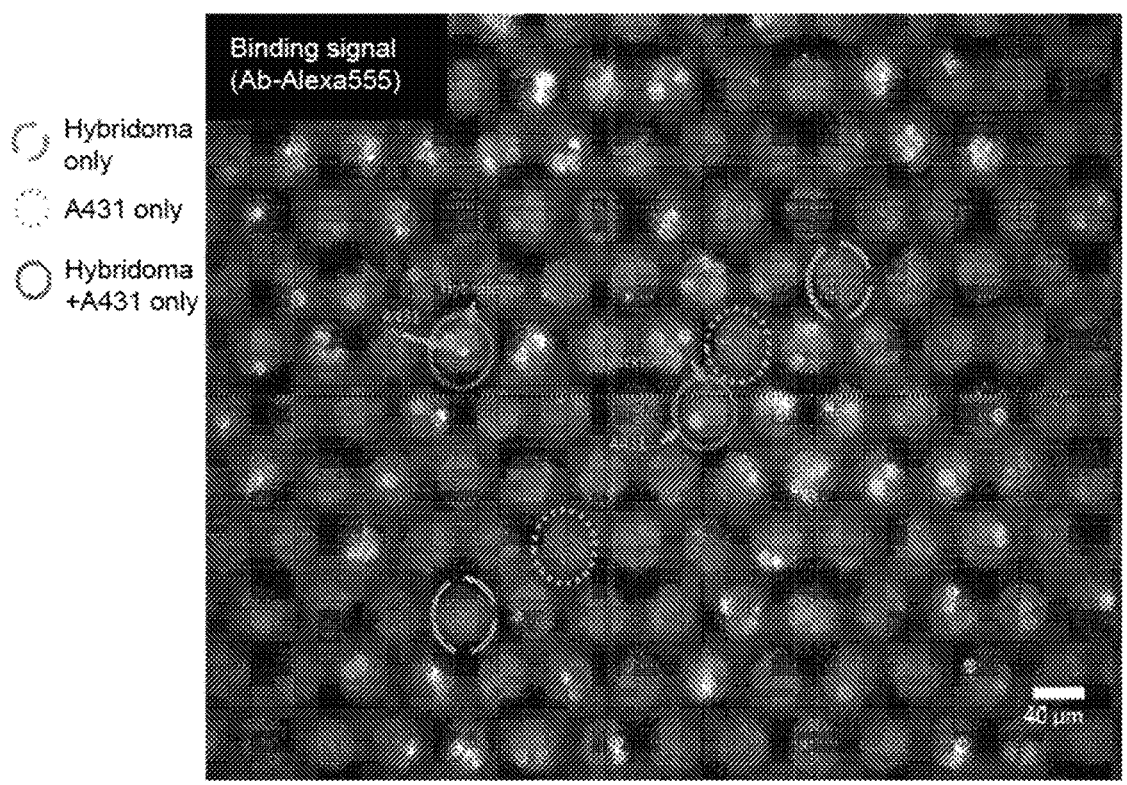

Sample Data:

FIGS. 2A-2C show images of a subsection of the microcapillary array showing either all of the cells (FIG. 2A, bright-field signal), A431 target cells (FIG. 2B, LiveGreen signal), or cells labeled with the fluorescent anti-mouse secondary antibody (FIG. 2C, Ab-a555 signal). Microcapillaries containing hybridoma cells that express antibodies specific for EGFR are indicated with two arrows in each image.

Figure 3:
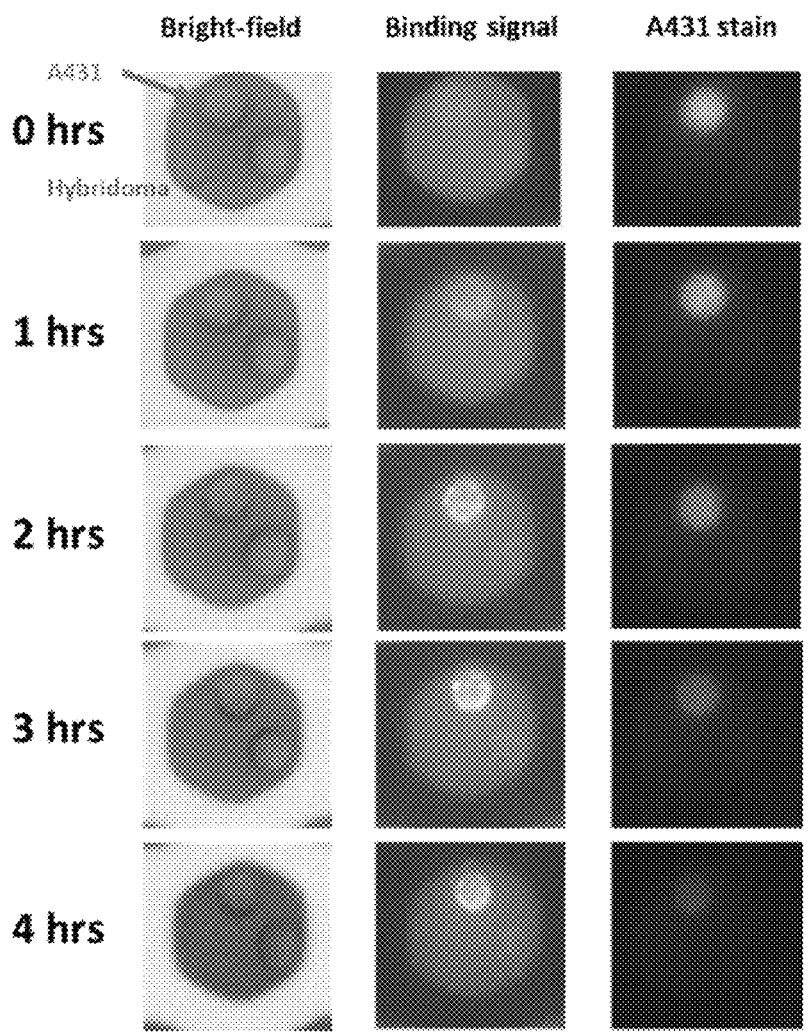
FIG. 3 shows images of a microcapillary containing both an A431 target cell and a hybridoma cell over the course of a 4 hour incubation.

FIG. 3 shows images of a microcapillary containing both an A431 target cell and a hybridoma cell over the course of a 4 hour incubation, where the antibody binding signal to the A431 target cells increased during the time course of the assay as mouse antibodies specific to EGFR are produced (middle column). LiveGreen staining of the A431 target cells declined over the same time period (right column).

Example 3. Yeast Library Screening Against Mammalian Cells

To determine the best secretion yeast plasmid vectors, a yeast vector library expressing scaffold proteins designed to bind to EGFR on a cancer cell surface was created. This library contained yeast cells with various soluble expression levels of a scaffold protein. Using the described assay, the variant expression library was screened to recover the plasmid vectors with high expression of the desired scaffold protein. In this experiment, the secreted scaffold has a c-Myc tag, which can be labeled with fluorescently-labeled antibodies.

Materials:
Cells:
  Yeast secretion library of scaffold proteins
  A431 cells (human cancer cell line expressing high levels of EGFR)
Detection Antibodies:
  Chicken anti-c-Myc
  Anti-chicken secondary antibody labeled with Alexa488
Media for Cell Culture:
  DMEM-10% FBS
  SD-CAA minimal yeast media
Reaction Buffer:
  SD-CAA minimal yeast media
Methods:
Cell line growth and preparation. The yeast library was grown in SD-CAA minimal yeast media (20 g dextrose; 6.7 g Difco yeast nitrogen base; 5 g Bacto casamino acids; 5.4 g $Na_2HPO_4$; 8.56 g $NaH_2PO_4 \cdot H_2O$; dissolved in deionized $H_2O$ to a volume of 1 liter). After growth, the yeast cells were washed twice with PBSA (phosphate-buffered saline+1 mg/ml BSA) and suspended in SD-CAA at a final concentration of 2,400 cells/uL.

The A431 cells were cultured in complete media (Dulbecco's Modified Eagle's Medium with 10% fetal bovine serum). The A431 cells were washed twice with PBSA and suspended in the SD-CAA containing yeast cells at a final concentration of 600 cells/uL.

Assay setup. Following mixing of the two cell types, two antibodies were added to the reaction mixture: 1:250 dilution of an unlabeled primary antibody (chicken anti-c-Myc) and 1:200 dilution of a labeled secondary antibody (anti-chicken Alexa488). This reaction mixture was then loaded into an ethanol-sterilized, corona-treated microcapillary array (40 μm diameter, 1 mm thick). A 2 mm slab of 1% weight/volume agarose was placed on the array to help prevent evaporation. After 18 hours of growth, the sample was imaged under fluorescence and bright-field microscopy.

Microcapillary array extraction. A Triton UV laser was used to extract the contents of desired capillaries. The laser operates for 18±2 ms (n=5 measurements), delivering a train of pulses at 2.5 kHz with a total energy of approximately 100 μJ. The microcapillary contents were extracted onto a glass coverslip, which was then placed in yeast growth media (liquid medium or agar plates) to propagate the extracted cells.

Sample Data

Figure 4A:
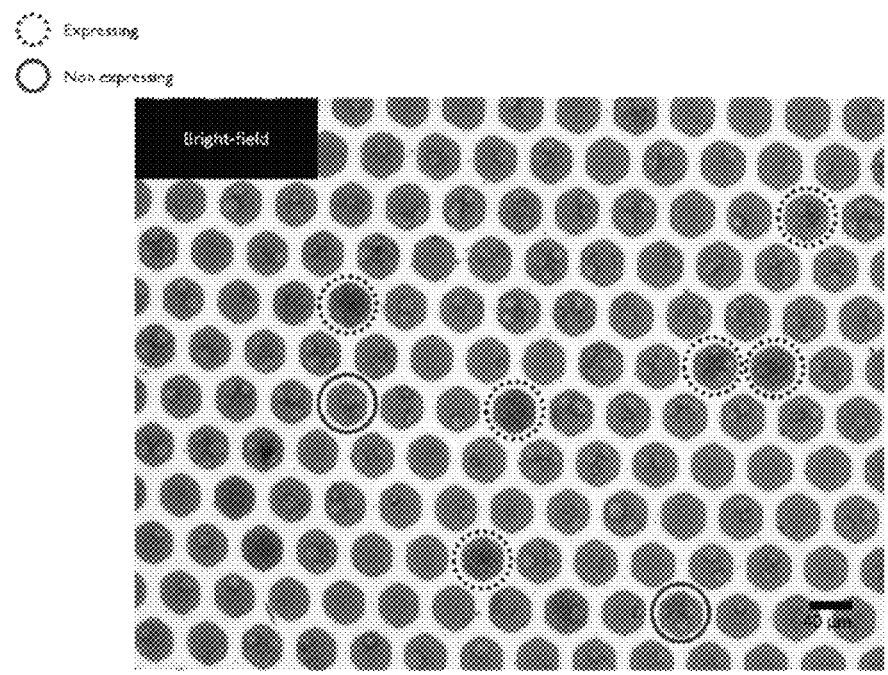
FIGS. 4A and 4B show images of a subsection of a microcapillary array highlighting expressing and non-expressing yeast cells against mammalian cells, where the cells are imaged using either bright-field (FIG. 4A) or a fluorescent antibody (FIG. 4B)
Figure 4B:
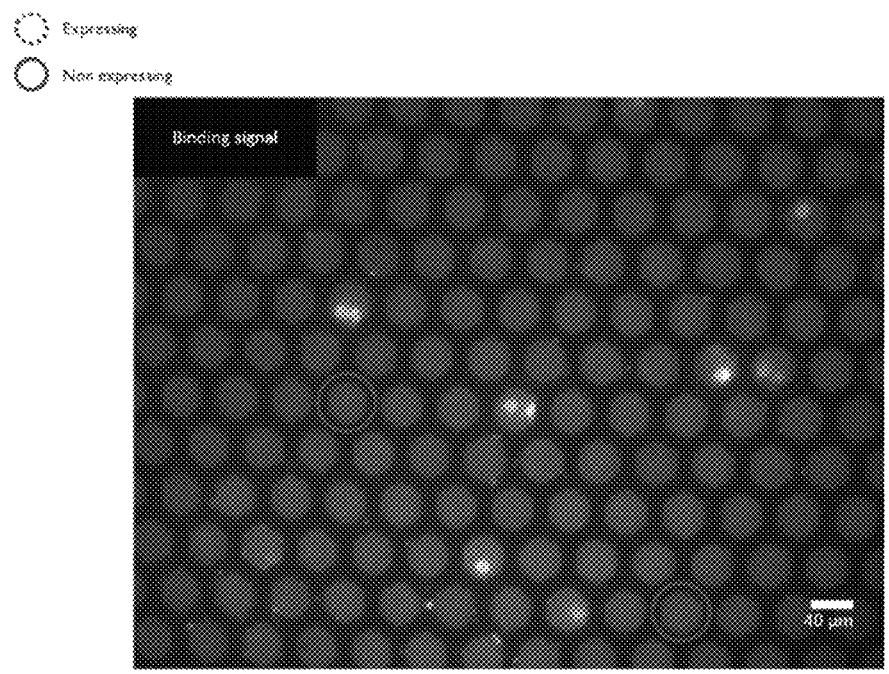

FIGS. 4A and 4B show images of a subsection of the microcapillary array that identifies microcapillaries with expressing and non-expressing cells using bright-field imaging (FIG. 4A) and fluorescence imaging (FIG. 4B).

Example 4. Growth of Cultured Human Cells in a Microcapillary Array

Figure 5A:
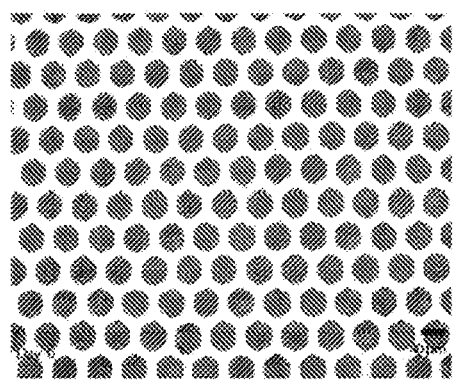
FIGS. 5A-5G illustrate the growth of an immortalized human cell in a microcapillary array over the course of 6 days.
Figure 5B:
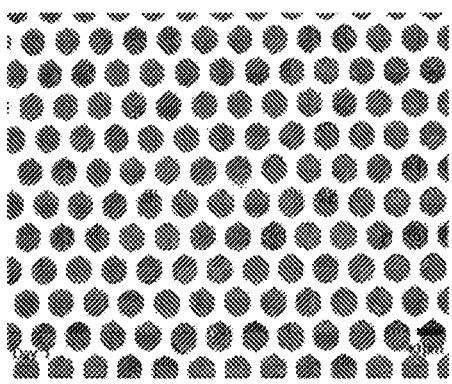
Figure 5C:
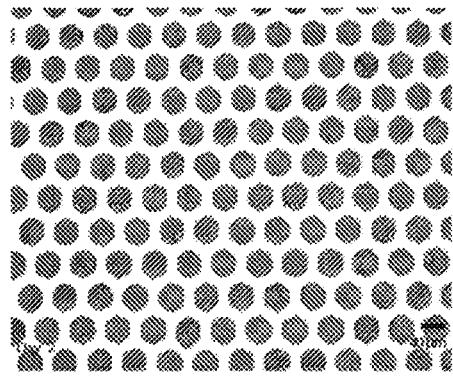
Figure 5D:
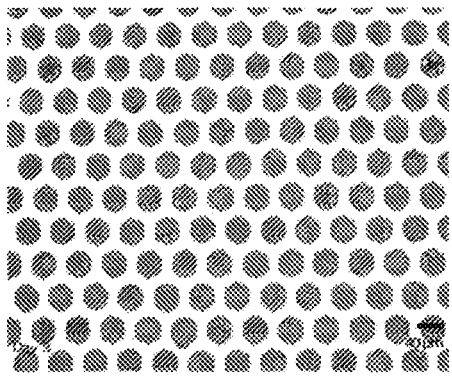
Figure 5E:
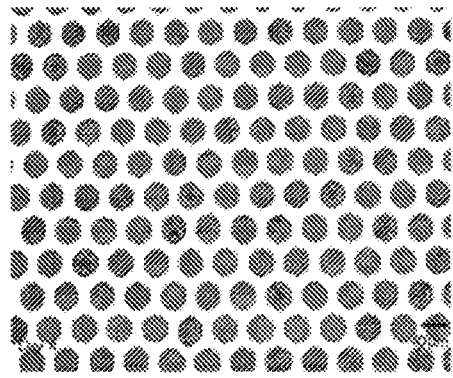
Figure 5F:
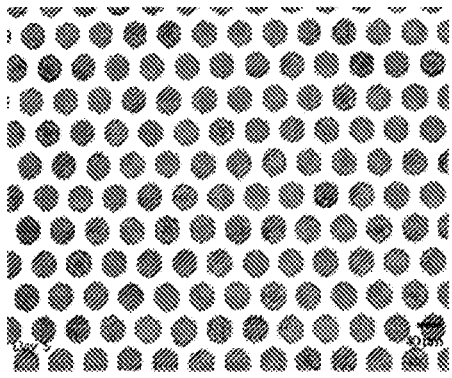
Figure 5G:
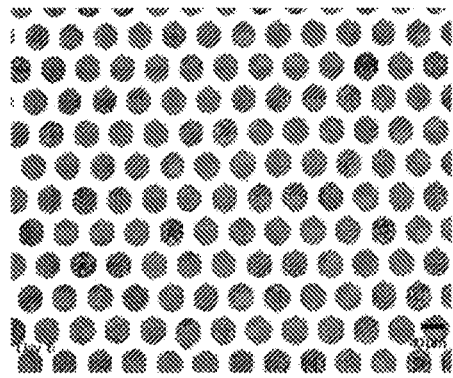

FIGS. 5A-5G demonstrate the growth of K562 cells (a human immortalized myelogenous leukemia cell-line) in growth media over the course of 6 days within an array of microcapillaries. A bright-field image of the same section of the array was taken every 24 hours. FIG. 5A: Day 0; FIG. 5B: Day 1; FIG. 5C: Day 2; FIG. 5D: Day 3; FIG. 5E: Day 4; FIG. 5F: Day 5; and FIG. 5G: Day 6. A 40 μm scale bar is shown in each image.

Example 5. Hybridoma Screening Against Mammalian Reporter Cells

To identify antibody variants that activate specific signaling pathways, hybridomas secreting different antibody variants are added into a microcapillary array with a reporter cell. For example, the reporter cell can be from Qiagen (see http://www.sabiosciences.com/reporter_assay_product/HTML/CCS-013L.html). If a protein variant binds the reporter cell and activates the signaling pathway, the reporter cell expresses a fluorescent protein. The signal fluorescence of activated cells is observed in microcapillaries that contain desirable protein variants and used to isolate the contents of those microcapillaries.

Example 6. Automated Cell Recovery System (ACRS)

This example describes a multi-stage sample recovery system that has been used to recover samples of interest from large-scale microcapillary arrays using the above-described screening methods. The Automated Cell Recovery System ("ACRS") is a configuration of 3 stages (1 x-y, and 2 linear stages) in two tiers working together to enable recovery of samples from a microcapillary array. The top X-Y stage holds the microcapillary array and moves the array around so that the entire array can be imaged by the microscope objective. The bottom two linear stages move the capture surface (for example an 18 well slide), so that the contents of a microcapillary of interest can be recovered into a separated recovery vessel (e.g., a new well of the 18 well slide). The entire configuration fits into the working distance of the microscope objective (7.4 mm), which enables the imaging of both the microcapillary array and the recovery array without removing any of the components from the microscope.

DETAILED DESCRIPTION

Figure 7A:
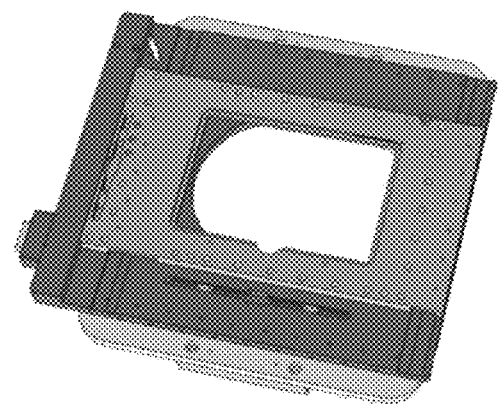
FIG. 7A illustrates an exemplary screening array stage.
Figure 7B:
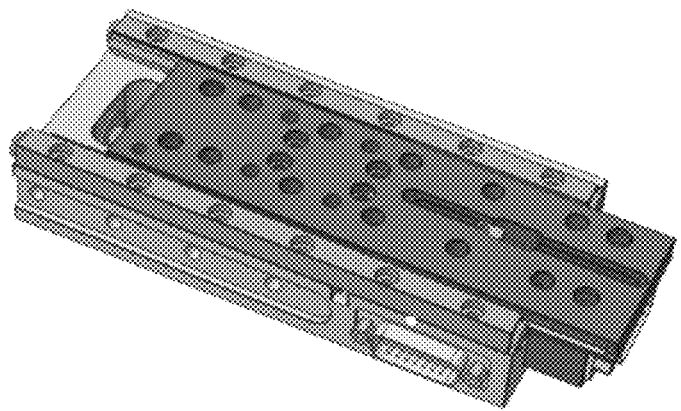
FIG. 7B illustrates an exemplary recovery array stage.

As noted above, the ACRS consists of an X-Y stage, as illustrated in FIG. 7A, and at least one X/Y stage, as illustrated in FIG. 7B. The stages interface with a Nikon Ti-E Motorized microscope or the like. The X-Y stage holds a screening array, such as an array of microcapillaries, and X/Y stage or stages are configured to hold a sample recovery array, such as an 18-well slide or the like.

Light from the associated microscope travels through both the tiers of stages for purposes of visualizing the contents of each sample in the screening array, for example each microcapillary in an array of microcapillaries held on the screening array stage. Because of the close proximity between the screening array stage and the recovery array stage, the objective is also able to image vessels associated with the recovery array, for example an 18-well slide.

These stages work independently of one another to position the desired microscale sample vessel, for example a microcapillary within an array of microcapillaries, and the desired capture surface, for example a recovery vessel within a recovery array, at the desired location relative to the microscope objective. For example, as illustrated in FIG. 8, if screening array 10 is found to contain three sample vessels of interest, for example the three sample vessels labeled 1, 2, and 3 in the drawing, the screening array stage is moved to position the first sample vessel in line with the light path of the extraction beam, and the recovery array stage is likewise independently moved to position the first recovery vessel of recovery array 14 in line with the light paths as shown in the top left panel of FIG. 8.

Figure 8:
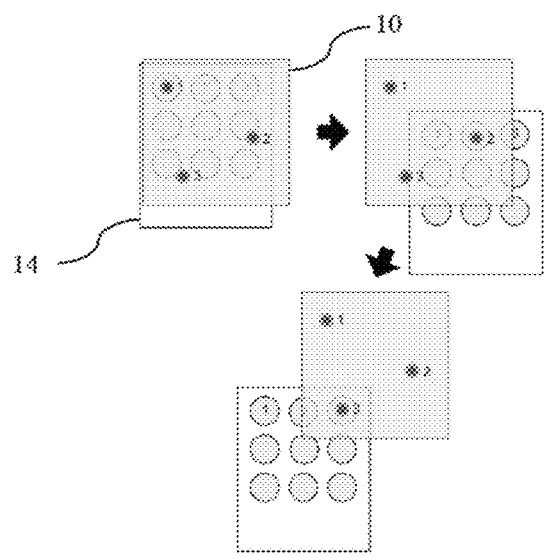
FIG. 8 shows exemplary positioning of a screening array and a recovery array relative to one another during the recovery of three samples of interest from the screening array, as facilitated by the instant sample recovery systems.

After the first sample of interest has been transferred into the first recovery vessel, the screening array stage is moved in the X and Y directions to position the second sample of interest in line with the extraction beam, and the recovery array stage is independently moved to position the second recovery vessel in line with the beam, as shown in the top right panel of FIG. 8. After the second sample of interest has been transferred into the second recovery vessel, the process is repeated by moving the screening array stage in the X and Y directions as necessary to position the third sample of interest in line with the extraction beam. The recovery stage is independently moved to position the third recovery vessel in line with the beam, as shown in the bottom panel of FIG. 8, and the sample is transferred into the third recovery vessel by the extraction beam.

In this example, only a single recovery array stage would be required in the system, because the first, second, and third recovery vessels are positioned in a straight line. If the user would like to use the other two rows of recovery vessels in the recovery array shown, the recovery array stage can be shifted manually, for example, to align the second row of recovery vessels with the extraction beam. Preferably, however, the system further comprises a second recovery array stage, positioned orthogonally to the first, for example as shown in the system of FIGS. 6A-6E, where the second linear stage automatically shifts the recovery array in a direction orthogonal to the direction of the first recovery array stage and thus enables the recovery of additional samples of interest into subsequent rows of the recovery array.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein, including all patents, patent publications, and other published references, are hereby incorporated by reference herein in their entireties and for all purposes to the same extent as if each individual publication or patent or patent application was specifically and individually indicated to be incorporated by reference in its entirety for all purposes.

What is claimed is:

1. A multi-stage sample recovery system comprising:
   a screening array stage, wherein the screening array stage is controllable in two dimensions relative to a microscope objective with a working distance of from 0.5 mm to 25 mm and which is configured for reversible association with a screening array;
   a first recovery array stage, wherein the first recovery array stage is controllable in at least one dimension relative to the microscope objective and is configured for reversible association with a recovery array;
   an extraction beam generator, wherein an extraction beam is directed from below the screening array stage,
   wherein the screening array stage and the first recovery array stage are controllable independently of one another.

2. The multi-stage sample recovery system of claim 1, wherein the extraction beam is optically coupled through an aperture in the screening array stage.

3. The multi-stage sample recovery system of claim 2, wherein the extraction beam is a laser beam.

4. The multi-stage sample recovery system of claim 1, further comprising a screening array reversible associated with the screening array stage.

5. The multi-stage sample recovery system of claim 4, wherein the screening array comprises a plurality of microscale sample vessels.

6. The multi-stage sample recovery system of claim 4, wherein the screening array stage comprises a plurality of microcapillaries.

7. The multi-stage sample recovery system of claim 6, wherein the screening array stage comprises at least 100,000, at least 300,000, at least 1,000,000, at least 3,000,000, or at least 10,000,000 microcapillaries.

8. The multi-stage sample recovery system of claim 1, further comprising a recovery array reversibly associated with the first recovery array stage.

9. The multi-stage sample recovery system of claim 8, wherein the recovery array comprises a plurality of recovery vessels.

10. The multi-stage sample recovery system of claim 8, further comprising a screening array reversible associated with the screening array stage.

11. The multi-stage sample recovery system of claim 10, wherein the recovery array comprises a plurality of recovery vessels.

12. The multi-stage sample recovery system of claim 10, wherein the screening array comprises a plurality of microscale sample vessels and the recovery array comprises a plurality of recovery vessels, and wherein the screening array and the recovery array are configured to position at least one microscale sample vessel and at least one recovery vessel within a working distance of the microscope objective.

13. The multi-stage sample recovery system of claim 8, wherein the recovery array comprises a recovery vessel.

14. The multi-stage sample recovery system of claim 13, wherein the recovery array comprises at least one recovery vessel, at least 3 recovery vessels, at least 10 recovery vessels, at least 30 recovery vessels, or at least 100 recovery vessels.

15. The multi-stage sample recovery system of claim 13, wherein the recovery vessel is configured to prevent cell damage or to promote cell growth.

16. The multi-stage sample recovery system of claim 13, wherein the recovery vessel is configured for an amplification reaction.

17. The multi-stage sample recovery system of claim 16, wherein the amplification reaction is a polymerase chain reaction.

18. The multi-stage sample recovery system of claim 16, wherein the amplification reaction is a reverse-transcription polymerase chain reaction.

19. The multi-stage sample recovery system of claim 13, wherein the recovery vessel is configured for a sequencing reaction.

20. The multi-stage sample recovery system of claim 8, wherein the recovery array is positioned below the screening array stage.

21. The multi-stage sample recovery system of claim 1, wherein the screening array stage and the first recovery array stage are controllable by an electronic motor.

22. The multi-stage sample recovery system of claim 21, wherein the electronic motor control is automated.

23. The multi-stage sample recovery system of claim 1, further comprising a second recovery array stage.

24. The multi-stage sample recovery system of claim 23, wherein the second recovery array stage is positioned orthogonally to the first recovery array stage.

* * * * *